United States Patent
Cekan et al.

(10) Patent No.: US 12,404,605 B2
(45) Date of Patent: Sep. 2, 2025

(54) METHOD FOR DIAGNOSING DISEASES USING MULTIPLEX FLUORESCENCE AND SEQUENCING

(71) Applicant: MultiplexDX, s.r.o., Bratislava (SK)

(72) Inventors: Pavol Cekan, Bratislava (SK); Evan Paul, Bratislava (SK)

(73) Assignee: MultiplexDX, s.r.o., Bratislava (SK)

( * ) Notice: Subject to any disclaimer, the term of this patent is extended or adjusted under 35 U.S.C. 154(b) by 1033 days.

(21) Appl. No.: 17/282,725

(22) PCT Filed: Oct. 7, 2019

(86) PCT No.: PCT/EP2019/076989
§ 371 (c)(1),
(2) Date: Apr. 2, 2021

(87) PCT Pub. No.: WO2020/070325
PCT Pub. Date: Apr. 9, 2020

(65) Prior Publication Data
US 2022/0002812 A1 Jan. 6, 2022
US 2023/0037279 A9 Feb. 2, 2023

(30) Foreign Application Priority Data
Oct. 5, 2018 (EP) .................................... 18198751
Oct. 5, 2018 (LU) ........................................ 100954

(51) Int. Cl.
C40B 30/04 (2006.01)
C12N 15/10 (2006.01)

(52) U.S. Cl.
CPC .......... *C40B 30/04* (2013.01); *C12N 15/1065* (2013.01)

(58) Field of Classification Search
None
See application file for complete search history.

(56) References Cited

U.S. PATENT DOCUMENTS

2006/0068434 A1 3/2006 Stoerker
2012/0115139 A1 5/2012 Kuroda et al.
(Continued)

FOREIGN PATENT DOCUMENTS

KR 2016-0147091 A 12/2016
WO 2013056217 A1 4/2013

OTHER PUBLICATIONS

Al-Maghrabi et al., "p53 Alteration and Chromosomal Instability in Prostatic High-Grade Intraepithelial Neoplasia and Concurrent Carcinoma: Analysis by Immunohistochemistry, Interphase In Situ Hybridization, and Sequencing of Laser-Captured Microdissected Specimens," Modern Pathology, vol. 14, No. 12, Dec. 2001, pp. 1252-1262.
(Continued)

*Primary Examiner* — Christian C Boesen
(74) *Attorney, Agent, or Firm* — Mueting Raasch Group

(57) ABSTRACT

The present invention relates to methods for diagnosing a disease by determining via multiplex fluorescence in situ hybridization (FISH) whether or not mRNA species and/or at least one miRNA species of disease-associated biomarkers are present in a sample obtained from a subject, and by determining by multiplex sequencing whether or not said mRNA species of disease-associated biomarkers and/or said miRNA species of disease-associated biomarkers of step(a) are present in said sample. The present invention also relates to kits for performing the methods for diagnosis as described and provided herein as well as use of such kits for performing the methods for diagnosis as described and provided herein.

16 Claims, 10 Drawing Sheets
Specification includes a Sequence Listing.

(56) References Cited

U.S. PATENT DOCUMENTS

2018/0326588 A1 11/2018 Van Rooyen
2020/0181710 A1 6/2020 Steelman

OTHER PUBLICATIONS

Iizuka et al., "Altered intracellular region of MUC1 and disrupted correlation of polarity-related molecules n breast cancer subtypes," Cancer Science, vol. 106, No. 3, Feb. 2015, pp. 307-314.
Lee, K., et al. (2011) "Precursor miR-886, a novel noncoding RNA repressed in cancer, associates with PKR and modulates its activity", RNA, 17(6): 1076-1089.
Canovas, A., et al. (2014) "Comparison of five different RNA sources to examine the lactating bovine mammary gland transcriptome using RNA-Sequencing", Scientific Reports, 4:1-7.
Hipp, J.D., et al., (2018) "Computer-Aided Laser Dissection: A Microdissection Workflow Leveraging Image Analysis Tools", Journal of Pathology Informatics, 9(1):1-9.
Kohda, Y., et al., (2000) "Analysis of segmental renal gene expression by laser capture microdissection", Kidney International, 57:321-331.
Chakraborty, C., et al., (2016) "Profiling cell-free and circulating miRNA: a clinical diagnostic tool for different cancers", Tumor Biol., 37:5705-5714.
Cox, M.L., et al., (2006) "Assessment of fixatives, fixation, and tissue processing on morphology and RNA integrity", Experimental and Molecular Pathology, 80:183-191.

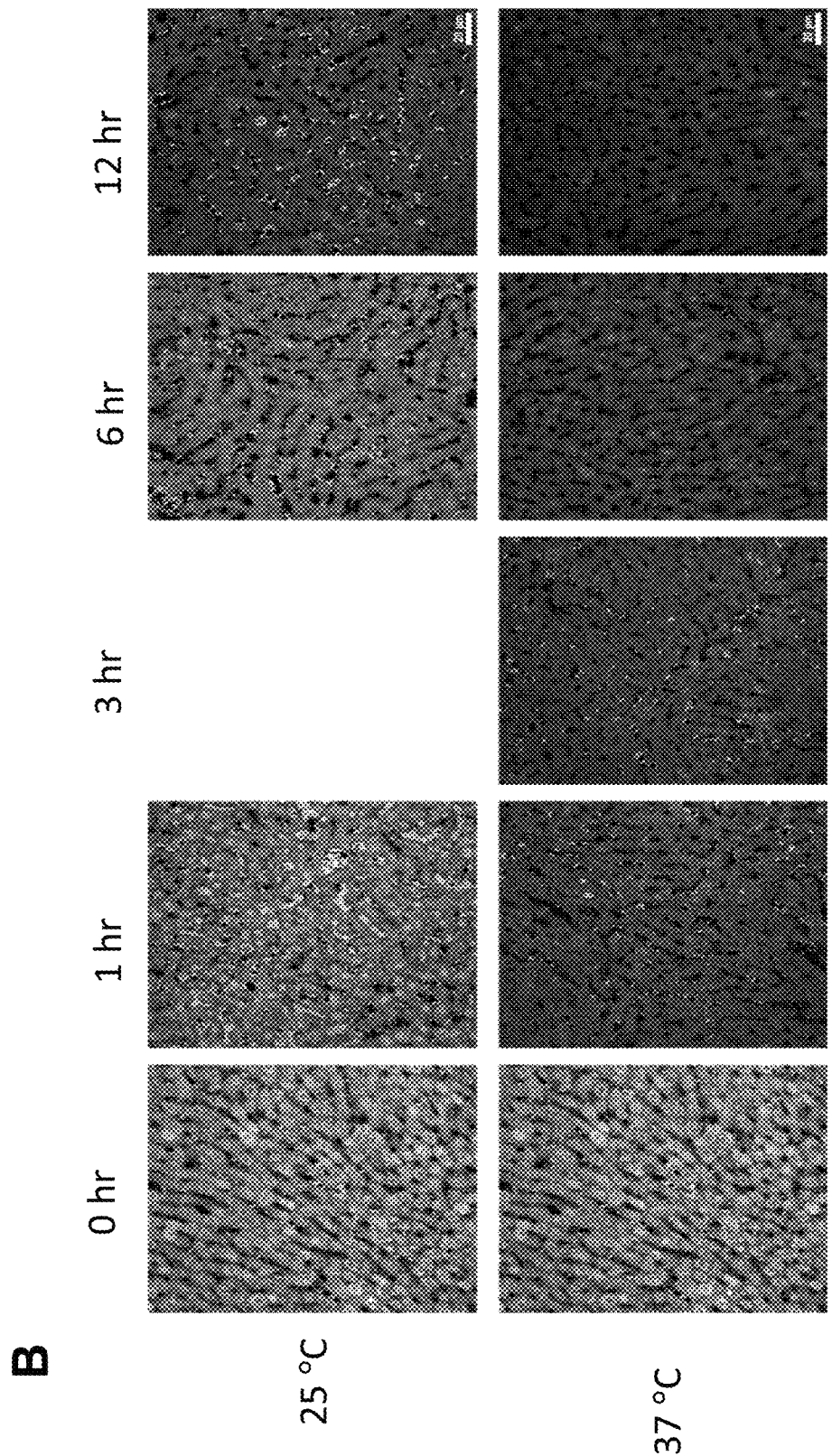

Figure 6:
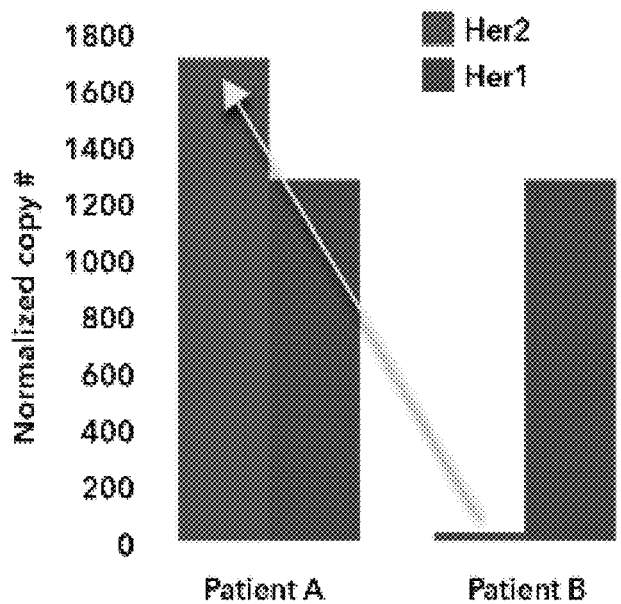
Figure 6:
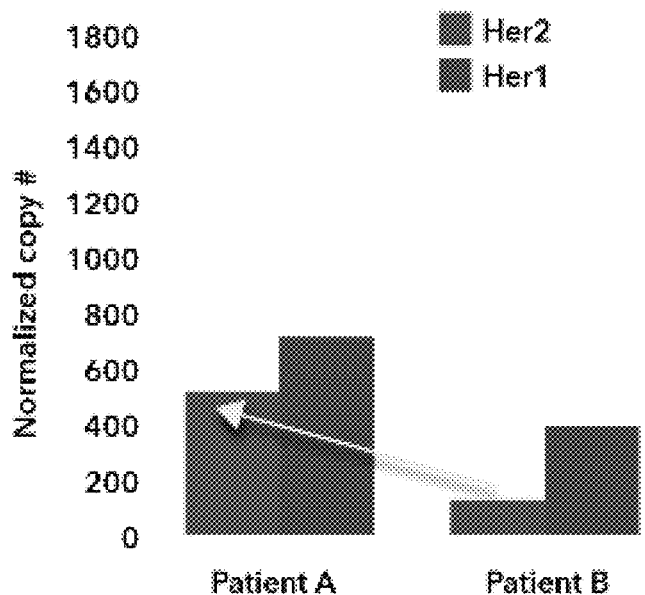

Figure 6
A
VISUALIZATION TEST
Her2: 51-fold increase in signal intensity
Her1: no increase in signal intensity
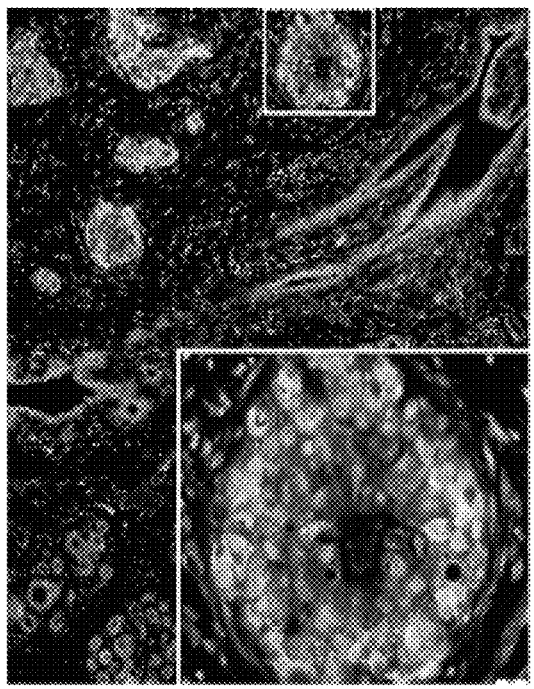
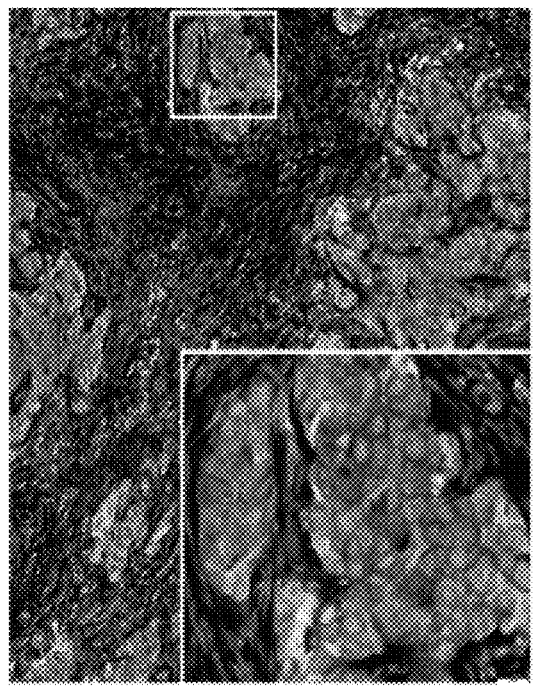
Her2  Her1  DNA (DAPI)
Patient A ≠ Patient B

B

SEQUENCING TEST + LASER MICRODISSECTION

Her2: 49-fold increase in copy #

Her1: no increase in copy #

Patient A ≠ Patient B

C

SEQUENCING TEST w/o LASER MICRODISSECTION

Her2: 4-fold increase in copy #

Her1: 2-fold decrease in copy #

Patient A = Patient B

Figure 7
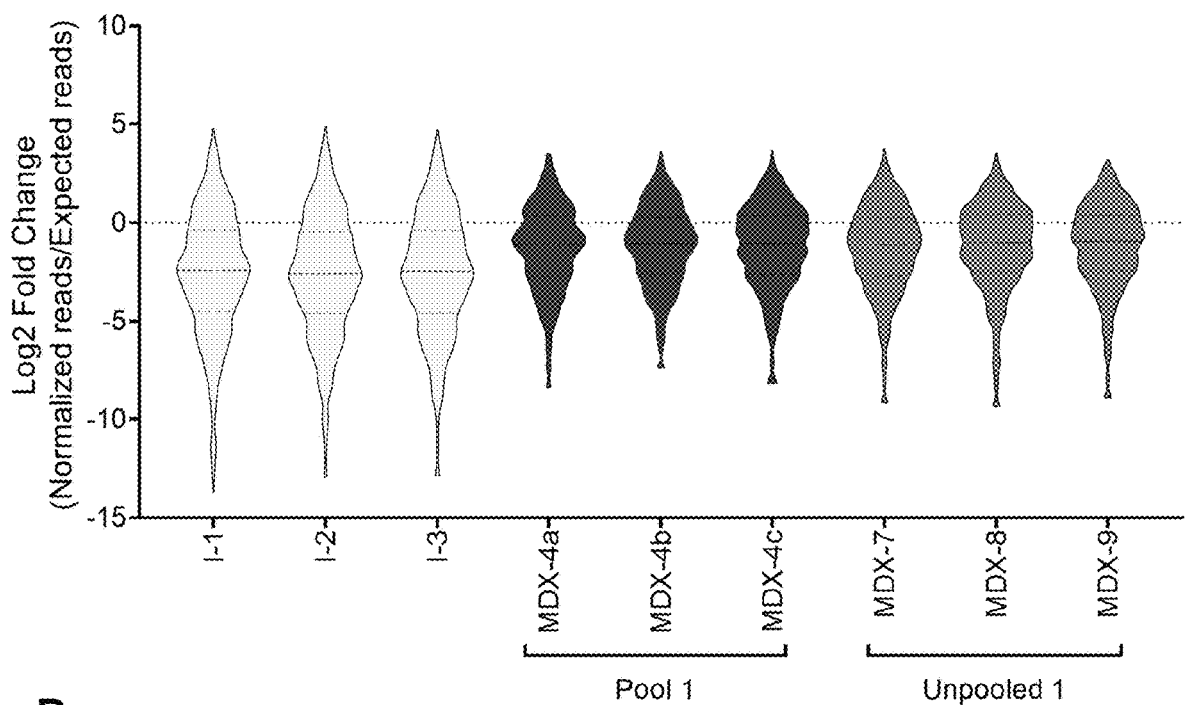
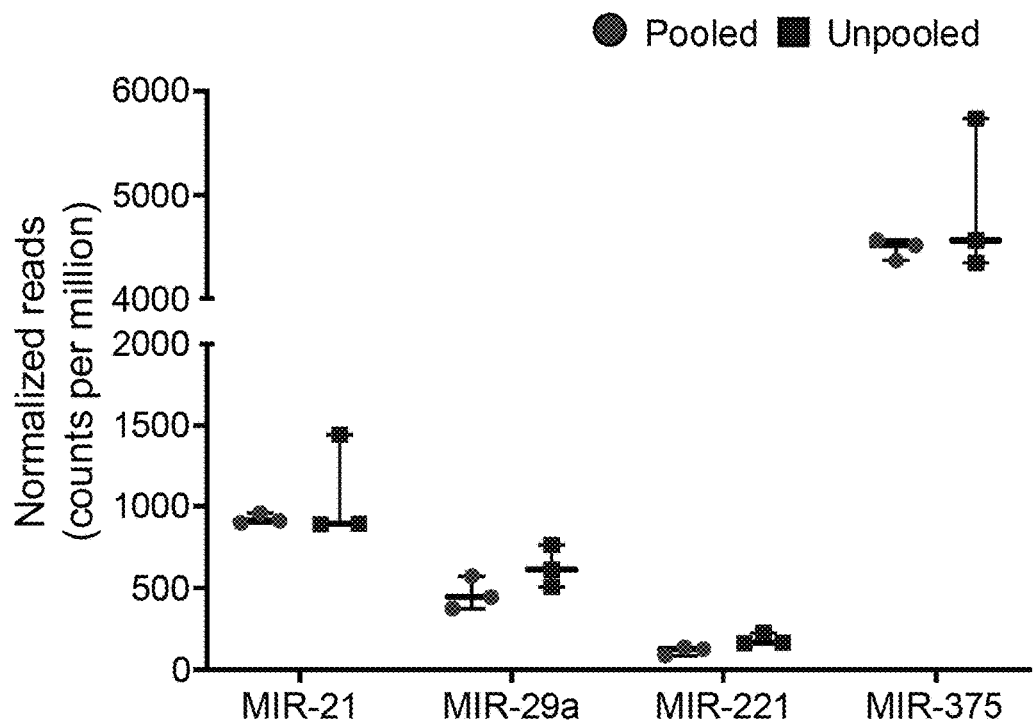

SEQUENCE LISTING

<160> NUMBER OF SEQ ID NOS: 16

<210> SEQ ID NO 1
<211> LENGTH: 20
<212> TYPE: DNA
<213> ORGANISM: Mus musculus

<400> SEQUENCE: 1
ggaaaagaaa ctaaccagga                                                   20

<210> SEQ ID NO 2
<211> LENGTH: 17
<212> TYPE: DNA
<213> ORGANISM: Mus musculus

<400> SEQUENCE: 2
atcagacccc agaaaag                                                      17

<210> SEQ ID NO 3
<211> LENGTH: 20
<212> TYPE: DNA
<213> ORGANISM: Mus musculus

<400> SEQUENCE: 3
ctaaggagtg tgtaacaact                                                   20

<210> SEQ ID NO 4
<211> LENGTH: 19
<212> TYPE: DNA
<213> ORGANISM: Mus musculus

<400> SEQUENCE: 4
ctgaaaatgg atggcgctg                                                    19

<210> SEQ ID NO 5
<211> LENGTH: 15
<212> TYPE: DNA
<213> ORGANISM: Mus musculus

<400> SEQUENCE: 5
cggaacggga cggga                                                        15

<210> SEQ ID NO 6
<211> LENGTH: 18
<212> TYPE: DNA
<213> ORGANISM: Mus musculus

<400> SEQUENCE: 6
agtcggtcct gagagatg                                                     18

<210> SEQ ID NO 7
<211> LENGTH: 16
<212> TYPE: DNA
<213> ORGANISM: Mus musculus

<400> SEQUENCE: 7
ggagcagaag ggcaaa                                                       16

<210> SEQ ID NO 8
<211> LENGTH: 17
<212> TYPE: DNA

```
<400> SEQUENCE: 8
tcagtacgag aggaacc                                                  17

<210> SEQ ID NO 9
<211> LENGTH: 20
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (3)..(3)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (10)..(10)
<223> OTHER INFORMATION: LNA residue
<220> FEATURE:
<221> NAME/KEY: misc_RNA
<222> LOCATION: (13)..(13)
<223> OTHER INFORMATION: LNA residue
<220> FEATURE:
<221> NAME/KEY: misc_RNA
<222> LOCATION: (16)..(16)
<223> OTHER INFORMATION: LNA residue

<400> SEQUENCE: 9
tcctggttag tttcttttcc                                               20

<210> SEQ ID NO 10
<211> LENGTH: 17
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (2)..(4)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (9)..(10)
<223> OTHER INFORMATION: LNA residue
<220> FEATURE:
<221> NAME/KEY: misc_RNA
<222> LOCATION: (13)..(13)
<223> OTHER INFORMATION: LNA residue
<220> FEATURE:
<221> NAME/KEY: misc_RNA
<222> LOCATION: (16)..(16)
<223> OTHER INFORMATION: LNA residue

<400> SEQUENCE: 10
cttttctggg gtctgat                                                  17

<210> SEQ ID NO 11
<211> LENGTH: 20
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (4)..(4)
```

```
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (13)..(13)
<223> OTHER INFORMATION: LNA residue
<220> FEATURE:
<221> NAME/KEY: misc_RNA
<222> LOCATION: (16)..(16)
<223> OTHER INFORMATION: LNA residue
<220> FEATURE:
<221> NAME/KEY: misc_RNA
<222> LOCATION: (18)..(19)
<223> OTHER INFORMATION: LNA residue

<400> SEQUENCE: 11
agttgttaca cactccttag                                              20

<210> SEQ ID NO 12
<211> LENGTH: 19
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (4)..(4)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (10)..(10)
<223> OTHER INFORMATION: LNA residue
<220> FEATURE:
<221> NAME/KEY: misc_RNA
<222> LOCATION: (13)..(13)
<223> OTHER INFORMATION: LNA residue
<220> FEATURE:
<221> NAME/KEY: misc_RNA
<222> LOCATION: (16)..(16)
<223> OTHER INFORMATION: LNA residue

<400> SEQUENCE: 12
cagcgccatc cattttcag                                               19

<210> SEQ ID NO 13
<211> LENGTH: 15
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (4)..(4)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (10)..(10)
<223> OTHER INFORMATION: LNA residue

<400> SEQUENCE: 13
tcccgtcccg ttccg                                                   15
```

```
<210> SEQ ID NO 14
<211> LENGTH: 18
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (6)..(6)
<223> OTHER INFORMATION: LNA residue
<220> FEATURE:
<221> NAME/KEY: misc_RNA
<222> LOCATION: (8)..(8)
<223> OTHER INFORMATION: LNA residue
<220> FEATURE:
<221> NAME/KEY: misc_RNA
<222> LOCATION: (13)..(13)
<223> OTHER INFORMATION: LNA residue
<220> FEATURE:
<221> NAME/KEY: misc_RNA
<222> LOCATION: (15)..(15)
<223> OTHER INFORMATION: LNA residue
<220> FEATURE:
<221> NAME/KEY: misc_RNA
<222> LOCATION: (17)..(17)
<223> OTHER INFORMATION: LNA residue

<400> SEQUENCE: 14
catctctcag gaccgact                                                 18

<210> SEQ ID NO 15
<211> LENGTH: 16
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (2)..(2)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
<221> NAME/KEY: misc_RNA
<222> LOCATION: (14)..(14)
<223> OTHER INFORMATION: LNA residue
<220> FEATURE:
<221> NAME/KEY: misc_RNA
<222> LOCATION: (16)..(16)
<223> OTHER INFORMATION: LNA residue

<400> SEQUENCE: 15
tttgcccttc tgctcc                                                   16

<210> SEQ ID NO 16
<211> LENGTH: 17
<212> TYPE: DNA
<213> ORGANISM: artificial
<220> FEATURE:
<223> OTHER INFORMATION: probe containing LNA
<220> FEATURE:
<221> NAME/KEY: misc_RNA
<222> LOCATION: (4)..(4)
<223> OTHER INFORMATION: LNA residue
<220> FEATURE:
<221> NAME/KEY: misc_RNA
<222> LOCATION: (6)..(6)
<223> OTHER INFORMATION: LNA residue
<220> FEATURE:
<221> NAME/KEY: misc_RNA
<222> LOCATION: (7)..(7)
<223> OTHER INFORMATION: LNA residue
<220> FEATURE:
```

```
<221> NAME/KEY: misc_RNA
<222> LOCATION: (9)..(9)
<223> OTHER INFORMATION: LNA residue
<220> FEATURE:
<221> NAME/KEY: misc_RNA
<222> LOCATION: (12)..(12)
<223> OTHER INFORMATION: LNA residue
<220> FEATURE:
<221> NAME/KEY: misc_RNA
<222> LOCATION: (16)..(16)
<223> OTHER INFORMATION: LNA residue

<400> SEQUENCE: 16
ggttcctctc gtactga                                                      17
```

METHOD FOR DIAGNOSING DISEASES USING MULTIPLEX FLUORESCENCE AND SEQUENCING

PRIORITY CLAIM

This application claims priority to International Application No. PCT/EP2019/076989, filed Oct. 7, 2019, which claims priority to European Application No. 18198751.2, filed Oct. 5, 2018, and to Luxembourg Application No. 100954, filed Oct. 5, 2018, wherein the contents of said applications are incorporated herein by reference in their entireties. Also, the entire contents of the ASCII text file entitled "IPM0116US Sequence Listing.txt" created on Apr. 1, 2021, and having a size of 6 kilobytes, is incorporated herein by reference.

The present invention relates to methods for diagnosing a disease by determining via multiplex fluorescence in situ hybridization (FISH) whether or not mRNA species and/or at least one, two, three, four, five, six, seven, eight, nine, ten, or more than ten miRNA species of disease-associated biomarkers are present in a sample obtained from a subject, and by determining by multiplex sequencing whether or not said mRNA species of disease-associated biomarkers and/or said miRNA species of disease-associated biomarkers of step (a) are present in said sample. The present invention also relates to kits for performing the methods for diagnosis as described and provided herein as well as use of such kits for performing the methods for diagnosis as described and provided herein.

Diagnosing diseases at an early state and as reliably as possible is of utmost importance for increasing successfulness of a subsequent therapy. Biomarkers have become increasingly important for diagnosis for all kinds of diseases, including biomarkers such as miRNAs (microRNAs). Suitable FISH methods for detecting abundant biomarkers such as miRNAs have been described earlier for detecting skin cancers (Renwick et al., JCI (2013), 123(6): 2694-2702). However, such methods have been developed for largely abundant and cell-type specific nucleic acids such as miRNAs and were not readily used for other biomarker nucleic acids. Furthermore, current FISH methods, including single molecule RNA FISH, do not ensure accurate transcript abundance measurements, especially when only signal intensity is quantified and used for biomarker quantification.

Breast cancer (BCa) is ranked 1st among all cancer types for women. 1 in 8 women will develop BCa in their lifetime with estimated 550 000 annual deaths worldwide in 2017. While in the US 44 000 women die of BCa, in Europe the situation is much worse with 143 000 deaths. Around 571 000 new patients were diagnosed in 2017 with invasive BCa in Europe. There are two major problems: 1. Current medical standards often don't allow re-diagnosis; 2. Today's diagnostic tests lack accuracy and precision providing false positive (20-30%), false negative (20-25%) and overdiagnosis (10-20%) results. Therefore, BCa patients are mis-/over-diagnosed, which results in mis-/under-/over-treatment of ca. 280 000 BCa patients (about 50%) seriously contributing to a high number of BCa deaths in Europe, also increasing social and economic burden of the patients and entire society.

Breast cancer (BCa) is the most common cancer in women, with 1.7 million new cases diagnosed worldwide in 2012. This number is expected to double in 2030, due to ageing, pollution, menopausal hormone use, lifestyle, obesity, etc. The incidence in Europe is ca. 0.6 million, affecting 1 in 8 women. BCa is the second leading cause of cancer death in women. Today, almost 50% of BCa patients are misdiagnosed and later mis-/under-/over-treated putting their lives to risk, often causing death. To improve this rate, BCa diagnosis and treatment need to be more precise and personalized. When a diagnosis of BCa is made, there are specific features of the disease that an oncologist needs to know, such as tumor size, node involvement, tumor grade, estrogen receptor status, progesterone receptor status, morphology, HER2/neu status, etc. These features create a picture of the cancer, which is then used to make a specific treatment plan for the patient. Often, this information is not clear enough to decide if chemotherapy will be effective. Oncologists have realized that 46% of BCa patients do not benefit from chemotherapy. If those patients (with no recurring BCa) get chemotherapy, it was possible that the side effects and possible complications would outweigh any benefit of the medications. Having 100% accurate BCa diagnostic data from a single diagnostic test, which directly defines the most effective therapy, treatment duration, and which patients benefit or not from chemotherapy would be beneficial for BCa diagnosis, prognosis and treatment.

However, there is only limited data provided in a single test: Conventional clinical protocols to diagnose BCa (IHC, H&E, blood tests, etc.) are not fully quantitative (incapable to precisely measure the levels of BCa markers). On the other hand, standard quantitative RNA-based methods (RT-qPCR, Microarrays, etc.) are performed on samples isolated from tissues to measure the expression level of BCa markers. However, they are only capable of measuring a few BCa markers and lack tissue-morphology information essential for treatment of heterogeneous BCa. Therefore, oncologists rely on limited numbers of clinically validated biomarkers to select BCa treatments and need to conduct several tests to obtain quantitative measurements and physical features. Thus, conventional diagnostics result in 31% cancer misdiagnosis plus 10-20% overdiagnosis.

Furthermore, there are unreliable diagnosis rates (~50%): Existing cancer profiling methods mostly do not reliably measure cancer markers. The HER2 status testing performed on tissue sections using IHC can generate false positive/negative rates (>30%). ER/PR false negative rates range from 20-25%, HER2 false positive rates are 20-30% and overdiagnosis is 10-20% (from both ISH and IHC). The cancer misclassification leads to unnecessary toxic treatment, often causing death.

Also, diagnosis is in most cases very lengthy (>4 weeks): To achieve the most precise diagnosis from current diagnostic tests, it requires conducting several tests (which is often not allowed by current medical standards), often involving different laboratories. This leads to a turnaround time of over a month, while generating a higher risk of false positive/negative rates. Other diagnostic solutions (Oncotype DX, MammaPrint, Prosigna) are slow in providing clinical information. It takes officially two weeks to receive results, but, those diagnostic tests eventually take longer than 4 weeks.

There are furthermore many cases of unnecessary chemotherapy (~46%): Due to very limited BCa profiling and prognostic tests, many BCa patients undergo needless chemotherapy—in 46% of BCa patients, chemotherapy is unnecessary.

These and further disadvantages need to be overcome. The present invention therefore addresses these needs and technical objectives and provides a solution as described herein and as defined in the claims.

The present invention relates to a method for diagnosing a disease, said method comprising:

(a) determining by multiplex fluorescence in situ hybridization (FISH) whether or not mRNA species and/or at least one, two, three, four, five, six, seven, eight, nine, ten, or more than ten miRNA species of disease-associated biomarkers are present in a sample obtained from a subject; and (b) determining by multiplex sequencing whether or not said mRNA species of disease-associated biomarkers and/or said miRNA species of disease-associated biomarkers of step (a) are present in said sample, preferably, wherein that part of said sample in which said mRNA species and/or at least one miRNA species of disease-associated biomarkers was determined in step (a) to be present is subject to laser capturing prior to performing step (b).

Laser capturing applied in the methods of the present invention is preferably laser capture microdissection. Laser microdissection allows the isolation of, e.g., distinct cells from samples, in particular tissue section samples based on visual selection. Visual selection may be computer and software aided. Visual selection includes, inter alia, slide scanning, RNA visualization, RNA biomarker quantification, spectral imaging, de-mixing, multiplexed visualization, whole-slide scanning, image analysis. Means and methods for laser capture microdissection are, for example, provided by Arcturus or Leica (see, e.g. Hipp et al., J Path Inform 2018; 9, 45).

Preferably, signals, such as fluorescence signals, immunohistochemical signals or signals from hematoxylin and/or eosin may be detected by microscopy when multiplex FISH is performed. Such microscopy may be automated, computer and/or software aided.

The present inventors observed that laser capturing significantly improved the results obtained by the methods of the present invention. Particularly, they observed (see FIG. 6) that laser capture microdissection reduces bias introduced by sampling heterogeneous tissues and ensures concordance between RNA FISH and RNA sequencing. Accordingly, it is preferred in the context of the methods of the present invention that, after having performed multiplex RNA FISH, that part(s) of the sample in which mRNA species and/or at least one miRNA species of disease-associated biomarkers was determined by RNA FISH to be present is/are subject to laser capturing, in particular laser capture microdissection prior to performing multiplex sequencing of RNA. By that, those parts of the sample showing signals in RNA FISH for one or more disease-associated biomarkers are, so to say, concentrated and subjected to a potential confirmation step by performing multiplex RNA sequencing. In fact, it is determined whether RNAs and/or miRNAs which was/were detected by multiplex RNA FISH may (again) be detected by multiplex RNA sequencing, thereby confirming the results obtained by multiplex RNA FISH. This two-step procedure avoids, e.g., false-positive and/or false-negative results obtained by RNA FISH and/or RNA sequencing, since RNAs and/or miRNAs which are detected by multiplex RNA FISH are required to be (re)detected by multiplex RNA sequencing.

In the context of performing the methods of the present invention, in particular laser capture microdissection, it is preferred that a sample, particularly a tissue section sample is placed on glass slides, preferably positively charged glass slides, frame slides, frame slides with PET membrane, or glass slides with membrane, Laser capture microdissection is preferably done as described in the appended examples.

A preferred sample used in the methods of the present invention is a tissue section sample. The tissue section sample may be formaldehyde fixed, flash frozen (FFFF) or formaldehyde fixed (FF) and/or paraffin embedded (PE), preferably formaldehyde fixed, paraffin embedded (FFPE). Formaldehyde fixation is preferably done by formalin which is a 37% aqueous solution of formaldehyde in water.

Preferably, a sample when used in the context of the present invention is obtained by microtome sectioning of a paraffin embedded sample which is preferably additionally formaldehyde fixed. Ideally and preferably, said sample obtained by microtome sectioning is after obtainment incubated at a temperature between 25° C. to 0° C.

Indeed, the present inventors found that it is advantageous to place a sample, preferably obtained by microtome sectioning after its obtainment, ideally immediately, at a temperature between 25° C. and 0° C., e.g., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., or 0° C., more preferably, 10° C., 9° C., 8° C., 7° C., 6° C., 5° C., 4° C., 3° C., 2° C., 1° C., or 0° C. Preferably, an ice-water bath may be used for incubating the sample at such a temperature.

Microtome sectioning is preferably done as described in the appended examples.

Figure 4:
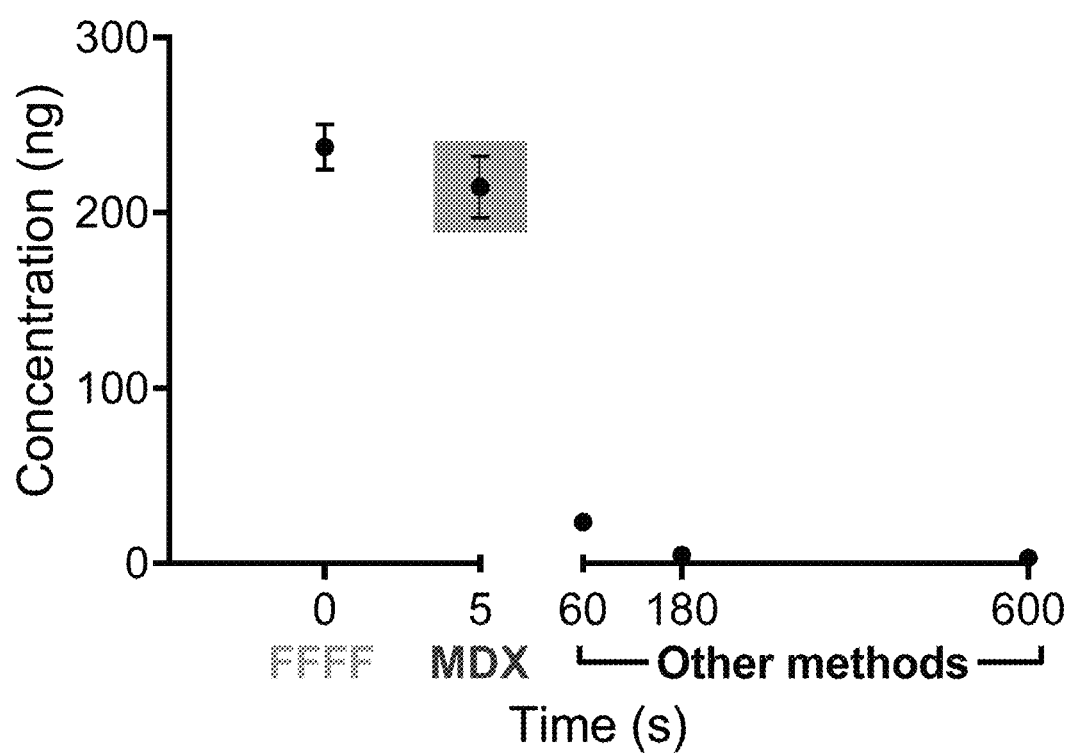

As is shown in FIG. 4, when placing a sample, preferably a tissue section sample, preferably formaldehyde fixed, paraffin embedded which is preferably obtained by microtome sectioning, after obtainment at a temperature between 25° C. to 0° C., achieved by an ice-cold water bath, diffusion of RNA, in particular small RNA, e.g., miRNA out of cells comprised by the sample is prevented, thereby ensuring high concentrations of RNA, in particular, small RNAs. Indeed, FIG. 4 shows a FFFF tissue sample which serves as baseline control. A sample which is preferably processed as described herein was placed after its obtainment through microtome sectioning at a temperature between 25° C. and 0° C., while samples prepared in accordance with the teaching of the prior art were not placed at such a cold temperature. In fact, the prior art does not teach placing a sample obtained through microtome sectioning at such a temperature. Rather, prior art teaches to immediately place a sample at a temperature of about 45° C. to 42° C. to flatten the microtome sectioned sample.

If a sample which may be paraffin embedded is to be diagnosed by the methods of the present invention, it is preferably deparaffinized prior to performing step (a) and/or step (b) of the methods as described herein. Deparaffinization is preferably achieved as described herein, in particular in the appended examples.

The present invention offers a novel personalized diagnostic test for several diseases, including but not limited to cancer (e.g., breast cancer (BCa)) which assesses the expression level of multiple biomarkers (mRNA and/or at least one, two, three, four, five, six, seven, eight, nine, ten, or more than ten different miRNA species). It combines visualization techniques (FISH) and subsequent multi-sample sequencing technologies in one single test with a high level of specificity and sensitivity. This reduces analysis biases and allows for simultaneous assessment of multiple RNA biomarkers (for example for BCa, e.g., 9 to 25 biomarkers) on a single patient's sample. The method of the present invention combines two independent qualitative/quantitative technologies, allowing cross-validation of biomarkers analysis, and eliminating or drastically reducing diagnostic errors. A specific personalised treatment and therapy length may then be suggested, as well as the probability of recurrence, which will help oncologists design a personalized and effective treatment. The inventive method described and provided herein may be applied for different diseases, particularly cancer, preferably any solid tumor (e.g., breast cancer) and any stage of cancer.

As defined herein, as used herein, the term "microRNA", "miRNA" or "miR" are used interchangeably and typically comprise non-coding RNA between 18 and 26 nucleobases in length, which may be the product of cleavage of a pre-miRNA by the enzyme Dicer. Examples of mature miRNAs are found in a miRNA database known in the art such as miRBase (microma.sanger.ac.uk).

As used herein and as known in the art, the term "mRNA" is used interchangeably with "messenger RNA" and means RNA molecules that convey genetic information from DNA to the ribosome, where they specify the amino acid sequence of the protein products of gene expression. mRNAs are unique for different genes and may exhibit specific expression patterns in different kinds of tissue such as, e.g., tumor tissue.

Generally, as used herein, the terms "polynucleotide", "nucleic acid" or "nucleic acid molecule" are to be construed synonymously. Generally, nucleic acid molecules may comprise inter alia DNA molecules (including cDNA, complementary DNA), RNA molecules (e.g., miRNA, mRNA, rRNA, tRNA, snRNA, siRNA, scRNA, snoRNA, and others as known in the art), LNA (locked nucleic acid) molecules (see, e.g., Kaur et al., Biochem (2006), 45(23): 7347-7355), oligonucleotide thiophosphates, substituted ribo-oligonucleotides or PNA (peptide nucleic acid) molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribosomal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules, which are complementary to the nucleic acid molecules described above and nucleic acid molecules, which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules, which can serve as primers.

As used herein, nucleic acid molecules may comprise different types of nucleotides, comprising naturally occurring nucleotides, modified nucleotides, and artificial nucleotides. Nucleotides as used herein generally comprise nucleosides, naturally occurring nucleosides, modified nucleosides, and artificial nucleosides. As known in the art, naturally occurring nucleosides comprise purine bases or pyrimidine bases. Examples for naturally occurring nucleosides comprise (deoxy)adenosine, (deoxy)guanosine, (deoxy)uridine, thymidine, and (deoxy)cytidine. Nucleosides as part of nucleotides (and, thus, nucleic acid molecules) as described herein may generally encompass structures comprising any purine or pyrimidine nucleoside and derivatives or analogues thereof. That is, "purine nucleoside" or "pyrimidine nucleoside" as used in context with the present invention generally comprises any kind of purine or pyrimidine as well as derivatives or analogues thereof as described herein respectively, as well as a sugar, e.g., a pentose. In one embodiment of the present invention, the purine nucleoside may be selected from the group consisting of (deoxy) adenosine, inosine, and (deoxy)guanosine and derivatives or analogues thereof. A derivative may be, e.g., a nucleoside with a purine selected from the group consisting of a deazapurine, an azidopurine, an alkylpurine, a thiopurine, a bromopurine, an O-alkylpurine, and an isopurine, for example a deazapurine such as, e.g., 7-deazapurine. That is, in one aspect of the present invention, the purine nucleoside may be a nucleoside with a purine selected from the group consisting of a deazapurine, an azidopurine, an alkylpurine, a thiopurine, a bromopurine, an O-alkylpurine, and an isopurine, for example a deazapurine such as, e.g., 7-deazapurine. In another aspect of the present invention, the purine nucleoside may be selected from the group consisting of 1-methyl(deoxy)adenosine, 2-methyl-(deoxy) adenosine, N-methyl(deoxy)adenosine, $N^6,N^6$-dimethyl(deoxy)adenosine, 7-deaza(deoxy)adenosine, 7-deaza-8-aza (deoxy)adenosine, 7-deaza-7-bromo(deoxy)adenosine, 7-deaza-7-iodo(deoxy)adenosine, 8-azido(deoxy)adenosine, 8-bromo(deoxy)adenosine, 8-iodo(deoxy)adenosine, 8-bromo-2'-deoxy(deoxy)adenosine, 2'-O-methyladenosin, inosin, 1-methylinosin, 2'-O-methylinosin, 1-methyl(deoxy) guanosine, 7-methyl(deoxy)guanosine, $N^2$-methyl(deoxy) guanosine, $N^2,N^2$-dimethyl-guanosine, isoguanosine, 7-deaza(deoxy)guanosine, 7-deaza-8-aza(deoxy)guanosine, 7-deaza-7-bromo(deoxy)guanosine, 7-deaza-7-iodo(deoxy) guanosine, 6-thio(deoxy)guanosine, $O^6$-methyl(deoxy) guanosine, 8-azido(deoxy)guanosine, 8-bromo(deoxy) guanosine, 8-iodo(deoxy)guanosine, 2'-O-methylguanosine, 8-azidoinosine, 7-azainosine, 8-bromoinosine, 8-iodoinosine, 1-methylinosine, and 4-methylinosine. In a further aspect of the present invention, the purine nucleosides may be selected from the group consisting of a queuosine, an archaeosine, a wyosine and a $N^6$-threonylcarbamoyladenosine. In one aspect of the present invention, the pyrimidine nucleoside may be selected from the group consisting of (deoxy)cytidine, (deoxy)thymidine, (deoxy)ribothymidine, (deoxy)uidine, and derivatives thereof. A derivative may be, e.g., a nucleoside with a pyrimidine selected from the group consisting of an alkylpyrimidine, a thiopyrimidine, a bromopyrimidine, an O-alkylpyrimidine, an isopyrimidine, an acetylpyrimidine hydropyrimidine, and a pseudopyrimidine. That is, in one aspect of the present invention, the pyrimidine nucleoside may be a nucleoside with a pyrimidine selected from the group consisting of an alkylpyrimidine, a thiopyrimidine, a bromopyrimidine, an O-alkylpyrimidine, an isopyrimidine, an acetylpyrimidine hydropyrimidine, and a pseudopyrimidine. In another aspect of the present invention, the pyrimidine nucleoside may be selected from the group consisting of 3-methyl-(deoxy)cytidine, $N^4$-methyl (deoxy)cytidine, $N^4,N^4$-dimethyl(deoxy)cytidine, iso(deoxy)cytidine, pseudo(deoxy)cytidine, pseudoiso(deoxy)cytidine, 2-thio(deoxy)cytidine, $N^4$-acetyl(deoxy)cytidine, 3-methyl(deoxy)uidine, pseudo(deoxy)urdine, 1-methylpseudo(deoxy)uridine, 5,6-dihydro(deoxy)uridine, 2-thio (deoxy)uidine, 4-thio(deoxy)uidine, 5-bromodeoxy(deoxy) uidine, 2'-deoxyuidine, 4-thio(deoxy)thymidine, 5,6-dihydro(deoxy)thymidine, $O^4$-methylthymidine, difluortoluene, and other nucleobase surrogates. As mentioned, the nucleosides as described and provided herein generally comprise a purine or pyrimidine or derivative or analogue thereof as described herein as well as sugar moiety such as, e.g., a pentose. Generally, the pentose as part of the purine or pyrimidine nucleoside or derivative or analogue thereof as described herein may be, inter alia, ribose, deoxyribose, arabinose, or methylribose (2-O-methyribose), for example, a ribose or a deoxyribose. That is, the nucleoside may be, e.g., a (ribosyl)nucleoside, a desoxy(ribosyl)nucleoside, an arabinosylnucleoside or an (methylribosyl)nucleoside, for example a (ribosyl)nucleoside or a deoxy(ribosyl)nucleoside.

As used herein, the terms "desoxy" and "deoxy" as prefixes of molecule terms are used synonymously and indicate the absence of an oxygen atom or a hydroxyl-group, e.g., in a given pentose such as ribose or others.

In context with the present invention, the presence of said disease-associated biomarkers in step(a) and step(b) is preferably indicative of said disease.

In a further embodiment of the present invention, the method described and provided herein allows the diagnosis of a disease on the presence or absence of said disease-associated biomarkers.

Generally, in context with the present invention, the disease to be diagnosed with the method described and provided herein may be any disease which is connected to the presence of specific biomarkers detectable with FISH and which can be sequenced. Accordingly, in a preferred embodiment of the present invention, such biomarkers are nucleic acid molecules, preferably miRNA or mRNA, most preferably mRNA molecules specific for the respective disease. In one embodiment of the present invention, the disease is cancer. In this context, the cancer may be any type of cancer, for example it is a solid cancer. Specifically, if the disease is cancer, it may be, e.g., solid cancer (e.g., on-small cell lung cancer, breast cancer, colorectal cancer, pancreatic cancer, ovarian cancer, skin cancer, prostate cancer, cancer of the brain or nervous system, head and neck cancer, testicular cancer, lung cancer, liver cancer, kidney cancer, bladder cancer, gastrointestinal cancer, bone cancer, cancer of the endocrine system, cancer of the lymphatic system, fibrosarcoma, neurectodermal tumor, mesothelioma, epidermoid carcinoma, or Kaposi's sarcoma), and blood cancer (e.g., leukemias). In a specific embodiment of the present invention, the disease is breast cancer (BCa).

In accordance with the present invention, the mRNA species to be detected by the method described and provided herein may be any mRNA whose elevated or reduced occurrence or expression is specific for a certain disease to be diagnosed as described herein. Its elevated or reduced occurrence or expression may also be typical for specific diseased tissue, e.g., tumor tissue (for cancer). For example, for breast cancer, typical mRNA species to be detected in accordance with the method of the present invention include those specific for HER2 (HER2, GRB7), Proliferation (Ki-67, STK15, Survivin, Cyclin B1, MYBL2), Oestrogen (ER, PR, Bcl2, SCUBE2), Invasion (Stromelysin 3, Cathepsin 12), and others (GSTM1, BAG1, CD68), where HER2, ER and PR represent the most relevant markers in accordance with the present invention. Further mRNA markers whose presence may be determined in accordance with the method of the present invention include: HER2, ER, PR (the most relevant breast cancer diagnosis/prognosis transcripts), NUPR1 (marker for taxol resistance), and CSF1 (marker for invasion in triple negative breast cancer cases). Accordingly, in one embodiment of the present invention, the mRNA species whose presence may be determined in accordance with the present invention may be selected from the group consisting of HER2, ER, PR, NUPR1, CSF1, GRB7, Ki-67, STK15, Survivin, Cyclin B1, MYBL2, ER, PR, Bcl2, SCUBE2, Stromelysin 3, Cathepsin L2, GSTM1, BAG1, and CD68, preferably including HER2, ER, and PR. Of course, in the methods of the present invention any mRNA which is a disease-associated biomarker can be assayed for its elevated or reduced occurrence as described herein.

In accordance with the present invention, the at least one, two, three or more, e.g., four, five, six, seven, eight, nine, ten, or more than ten miRNA species to be detected by the method described and provided herein may be any miRNA whose elevated or reduced occurrence or expression is specific for a certain disease to be diagnosed as described herein. Its elevated or reduced occurrence or expression may also be typical for specific diseased tissue, e.g., tumor tissue (for cancer). For example, for breast cancer, typical miRNA species to be detected in accordance with the method of the present invention include miR-21, miR-29a, miR-221, and miR-375. Accordingly, in one embodiment, the at least one, two, three, four, five, six, seven, eight, nine, ten, or more than ten miRNA species whose presence may be to be determined in accordance with the present invention may be selected from the group consisting of miR-21, miR-29a, miR-221, and miR-375. Of course, in the methods of the present invention any miRNA which is a disease-associated biomarker can be assayed for its elevated or reduced occurrence as described herein.

In one embodiment of the present invention, step(a) further comprises determining by multiplex FISH whether or not snRNA (small nuclear RNA) species and/or scRNA (small conditional RNA) species of disease-associated biomarkers are present in said sample. In accordance with the present invention, the snRNA or scRNA species to be detected by the method described and provided herein may be any snRNA or scRNA whose elevated or reduced occurrence or expression is specific for a certain disease to be diagnosed as described herein. Its elevated or reduced occurrence or expression may also be typical for specific diseased tissue, e.g., tumor tissue (for cancer). For example, for breast cancer, typical snRNA or scRNA species to be detected in accordance with the method of the present invention include U2 snRNA and 7SL scRNA (the novel biomarker-pair for the main breast cancer subtypes). Accordingly, in one embodiment, the snRNA or scRNA species whose presence may be determined in accordance with the present invention may be selected from the group consisting of U2 snRNA and 7SL scRNA. Of course, in the methods of the present invention any snRNA or scRNA which is a disease-associated biomarker can be assayed for its elevated or reduced occurrence as described herein.

Furthermore, in accordance with the present invention, the presence of control markers may be determined by multiplex FISH in step(a). In one embodiment of the present invention, the presence of additionally one or more RNAs selected from the group consisting of 28S rRNA, poly(A) RNA, Beta-actin, GAPDH, RPLPO, GUS, and TFRC may be determined by FISH as control.

In a further embodiment of the present invention, step(b) further comprises determining by multiplex sequencing whether or not snRNA and/or scRNA species of disease-associated biomarkers are present in said sample. In a preferred embodiment in this context, step(b) further comprises determining by multiplex sequencing whether or not snRNA and/or scRNA species of disease-associated biomarkers are present in said sample if also step(a) further comprises determining by multiplex FISH whether or not snRNA (small nuclear RNA) species and/or scRNA (small conditional RNA) species of disease-associated biomarkers are present in said sample.

In context with the present invention, in a first step of the method described and provided herein, multiplex fluorescence in situ hybridization (FISH) is used to determine whether or not mRNA species and/or at least one, two, three, four, five, six, seven, eight, nine, ten, or more than ten miRNA species of disease-associated biomarkers are present in a sample obtained from a subject. As used herein, "multiplex FISH" is a FISH assay as known to the person skilled in the art (cf., e.g., Lee et al., RNA (2011), 17(6): 1076-1089) where the presence of an mRNA and/or at least one, two, three, four, five, six, seven, eight, nine, ten, or more than ten different miRNA species is determined. In one embodiment of the present invention, the presence of several mRNAs, scRNAs, snRNAs, rRNAs, other RNAs, and/or at least one, two, three, four, five, six, seven, eight, nine, ten, or more than ten miRNA species is determined by "multiplex" FISH assay simultaneously. In accordance with the present invention, simultaneous FISH measurement of different RNA species may result in multi-color FISH as different RNA species may be detected using different dye labels.

Preferably, multiplex RNA FISH is done as described in the appended examples.

For example, particularly where the disease to be diagnosed by the inventive method is breast cancer, in one embodiment of the present invention, the presence of at least one, two, three, four, five, six, seven, eight, nine, ten, or more than ten mRNAs (HER2, ER, PR) is determined simultaneously. In another embodiment of the present invention, additionally to mRNA of HER2, ER and/or PR, the presence of (i) U2 snRNA and/or 7SL scRNA, (ii) 28SrRNA and/or poly(A) RNA (as controls and malignancy reporters), (iii) NUPR1 (taxol resistance marker), and/or (iv) CSF1 (marker for invasion in triple negative breast cancer) is determined by multiplex FISH simultaneously.

In another embodiment of the present invention, particularly where the disease to be diagnosed by the inventive method is breast cancer, the presence of up to 25 biomarkers is determined by multiplex FISH simultaneously: mRNA related to HER2 (HER2, GRB7) and/or to oestrogen (ER, PR, Bcl2, SCUBE2), as well as one or more of the RNAs related to any of the following clusters: proliferation (Ki-67, STK15, Survivin, Cyclin B1, MYBL2), invasion (Stromelysin 3, Cathepsin 12), reference (Beta-actin, GAPDH, RPLPO, GUS, TFRC), miRNA (at least three of any one of miR-21, miR-29a, miR-221, or miR-375), and/or others (GSTM1, BAG1, CD68).

Generally, in context with the present invention, the diagnostic method described and provided herein is performed starting from a patient's tissue (e.g., cancer tissue, such as BCa tissue) removed during biopsy or surgery. Tissues are first analysed by multiplex FISH assay allowing the simultaneous visualization and quantification of several (up to 9-25 in BCa) representative biomarkers. The assay is based on fluorescently labelled nucleic-acid probes (available from, e.g., MultiplexDX®) which recognize selected mRNA or miRNA targets. The hybridization of FISH probes to RNAs allows the visualization of the biomarkers within single cells by common fluorescent microscopy. In one embodiment of the present invention, the present invention may use "click labelling" to increase the binding affinity of FISH probes based on the chemical fusion of two closely neighbouring probes on a specific RNA target (cf. FIG. 2). Accordingly, it is preferred that probes used for fluorescence in situ hybridization (FISH) of RNA may be conjugated by click chemistry. Click chemistry cross-linking of probes is preferably done as described in the appended examples. In accordance with the present invention, the specificity of FISH probes allows the detection of multiple biomarkers (multi-color FISH) simultaneously (multiplex FISH) and precise biomarkers' quantification derived from FISH signal intensity.

As known to the person skilled in the art, in FISH, any relatively stable mis-hybridization to abundant RNAs will result in false-positive signals which reduce specificity. Although probe hybridization in FISH assays cannot be directly compared to hybridization of primers or siRNAs in PCR or RNAi, respectively, it is clear that during PCR, the end of primers, whose perfect binding is necessary for starting the enzymatic chain reaction, is the most sensitive for any mismatch or bulge within primer-target duplex resulting in an aberrant PCR reaction. While 1% mis-hybridization of siRNAs to abundant RNAs such as ribosomal RNA (rRNA) is irrelevant, such a level of mis-hybridization to abundant off-target transcripts in RNA FISH would result predominantly in rRNA signal (since rRNA is at least 1000-100,000 times more abundant than mRNAs, 1% mis-hybridization to rRNA would be up to 1,000 times higher than target mRNA signal). Thus, probe mis-hybridization remains a large technological barrier.

Probes to be employed in the inventive method described herein may be of any kind suitable for application in FISH as known in the art. Preferably, the probe is based on a nucleic acid molecule. In one embodiment of the present invention, the probe is an LNA molecule. The probe can be of any length, dependent on the RNA molecule whose presence is to be determined according to the method of the present invention. For example, in one embodiment of the present invention, the probe may be up to 40 nucleotides in length, preferably up to 35, 30 or 20 nucleotides. In an additional embodiment of the present invention, the probe is at least 7 nucleotides in length, preferably at least 8, 9 or 10 nucleotides.

Probes for RNA detection in FISH can be designed as commonly known in the art. For example, in accordance with the present invention, the following parameters are pre-set: 1. A target sequence (RNA of interest), 2. Hybridization temperature of RNA FISH protocol, and, 3. The desired number of FISH probes per target. A list of sequences that can be subsequently inserted into the synthesis program of a DNA synthesizer may then be generated by a program provided by MultiplexDX® or other commercially available programs. Based on predicted hybridization behaviors and the least cross-hybridization to the most abundant RNAs (e.g. rRNAs, ncRNAs, tRNAs, mt-RNAs, scRNAs, etc.), an appropriate sequence for the probe may be selected. In accordance with the present invention, optimal probes may fulfil the following characteristics: (a) minimized cross-hybridization to the most abundant RNAs, and (b) equalized LNA/DNA probe melting temperatures ($T_M$s)/binding affinities by varying probe lengths, exact positioning of probes, and LNA content per probe. Based on the chosen hybridization conditions, RNA FISH probes may be, e.g., 11- to 15-nt long locked nucleic acid (LNA)-modified DNA probes (LNA/DNA) with ~3 to 5 LNA modifications per probe. $T_M$ prediction may be based on algorithms currently used by, e.g., IDT DNA oligo analyzer for DNA/DNA, DNA/RNA, and LNA/DNA duplexes, taking target type (DNA or RNA), oligo concentration, and $Na^+$ concentration as the main input parameters. Optionally, this may be modified in accordance with the present invention for 50% Formamide, which may be used in RNA FISH protocols as a denaturant.

For the multiplex FISH as to be employed in context with the method of the present invention, for example short, fluorescent, multi-labeled LNA/DNA probes (about 11-15 nt long, about 4-8 fluorophores per probe, about 20-50 probes per target) may be used for visualization of any RNA target (up to 5 kb). The probes may be, e.g., synthesized, deprotected, and desalted on an automated Dr. Oligo 48 (cf. www.biolytic.com/t-dr-oligo-48-dna-rna-oligo-synthesizer-.aspx) or Dr. Oligo 768 (cf. www.biolytic.com/t-dna-rna-oligo-synthesizer.aspx) DNA/RNA synthesizer or other means known in the art, each with several desired modifications if required. Each fluorescent multi-labeled probe (e.g., about 11-15 nt) may be prepared with an elongation segment containing multiple (4-8) 5-Octadiynyl-dU or Abasic-Alkyne or other suitable dye, each separated by, e.g., 5-nt segment or C18 spacer (GlenResearch). In accordance with this invention, this allows very powerful, selective and efficient click chemistry labelling with azide-labeled fluorophores or any fluorophore of interest (e.g., ATTO-, Alexa-, Cy, BODIPY-, DyLight-, Cyto-, Seta-, RadiantDy- and CF-dyes selecting some of the brightest, the most photo- and water-soluble, avoiding unspecific protein binding). Click chemistry, due to its robust specificity and quantitative efficiency when compared to NHS-ester chemistry, is in accordance with the present invention a suitable approach to enable multiple labelling of the probes with 5 or more fluorophores per probe. Comparing click chemistry labeling to NHS-ester labeling, even though fluorophore-azides are 33-50% more expensive than fluorophore-NHS esters, in accordance with the present invention usually only 1.2× excess of azide may be used, but about, e.g., 10× excess of NHS-ester in labeling reaction with oligo, making click chemistry more cost-efficient.

In accordance with the present invention, the multiplex FISH as to be employed in the inventive method described and provided herein, may be for example performed as follows. In one embodiment, tissue cells may be fixed prior to detection of biomarkers as described herein. Suitable methods for cell and tissue fixation and subsequent biomarker detection are known in the art and also described in, e.g., U.S. Pat. Nos. 9,359,636, 9,005,893 and 8,394,588. In accordance with the present invention, by in situ click ligation of two closely neighboring probes (ca. 15-nt long), a more stable 30-nt long double-probe may be formed (cf. FIG. 2), followed by mishybridization-targeting stringent wash, which will wash-off mishybridized probes completely and reduce background while preserving perfect specific binding of all probes (cf. FIG. 2). This allows to achieve specific RNA FISH signals of even low abundant RNA targets.

As described above, it is preferred that a sample is fixed prior to performing step(a) of the methods as described herein. Fixation may preferably be achieved by treatment with 1-ethyl-3-(3-dimethylaminopropyl)carbodiimide (EDC) or 5-ethylthio-1H-tetrazole (ETT). That said, fixation is preferably done as described herein, in particular in the appended examples.

Figure 2:
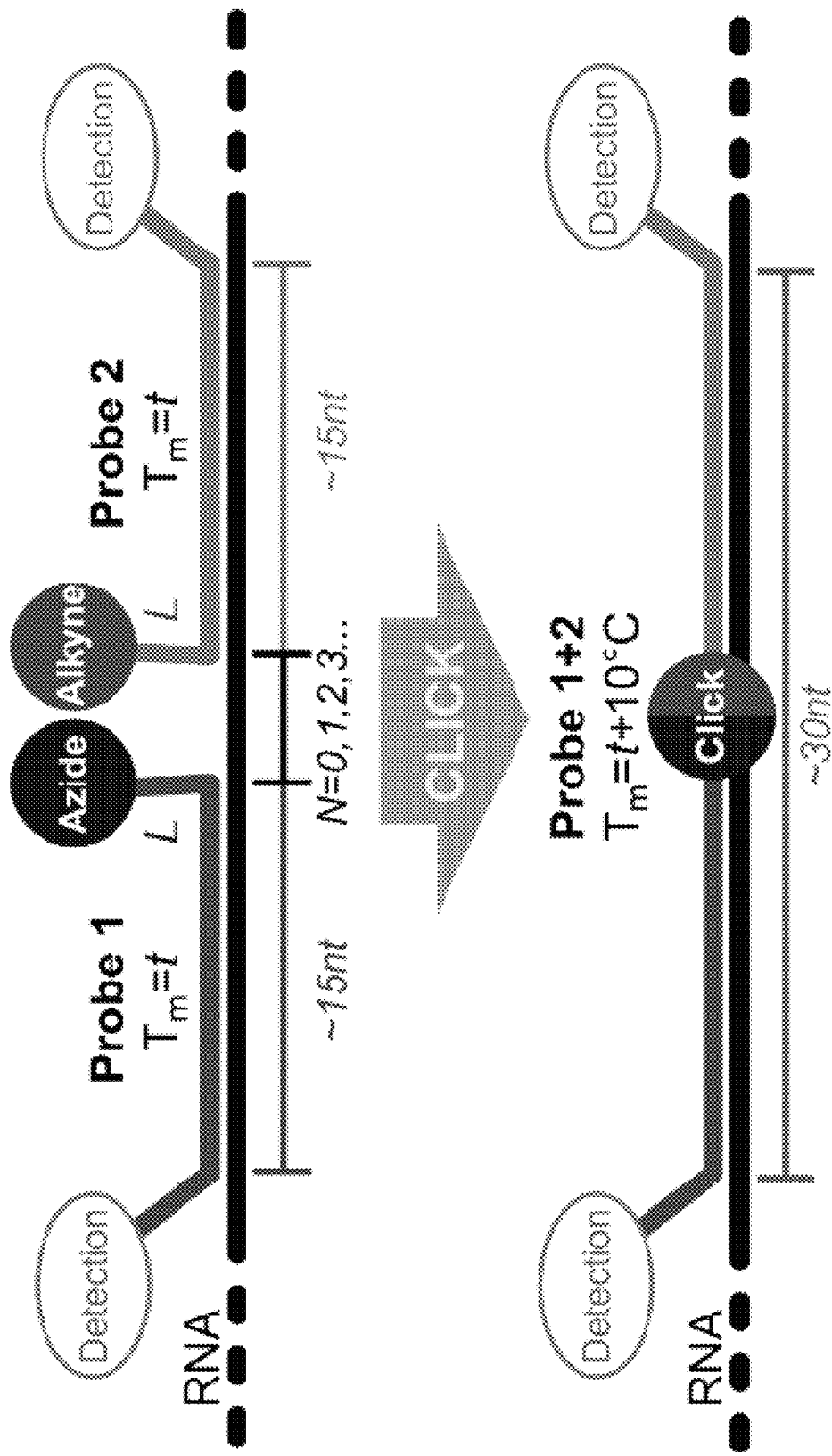

As regards click-labelling as described in context with the present invention, for example, one probe may be labeled with azide (through 3'-amino-modified LNA/DNA oligonucleotide), and another may be tagged with alkyne on the 5'-end, directly labeled in oligonucleotide synthesis (cf. FIG. 2). Each probe may preferably be labelled with the same fluorophore. This approach was tested in vitro as shown in FIG. 2. Then, click chemistry may be performed at room temperature to conjugate the probes. This significantly increases binding affinity of the formed double-probe. This in turn may enable use of mishybridization-targeting stringent wash, which washes-off mishybridization coming from 15-nt long probes completely by increasing temperature of the wash above previous hybridization temperature (e.g., if hybridization temperature is 40° C., then the stringent wash may be 45-50° C.). Increased stability of the double-probe following conjugation and the stringent wash may preserve perfect and specific binding of all probes. In accordance of the present invention, multiplex FISH approach may be performed as follows: 1. RNA FISH using 15 nt long LNA/DNA probes at 40° C.; 2. Cool down and click-chemistry performed at room temperature; 3. Stringent wash at 45-50° C. (5-10° C. above previous hybridization temperature).

Figure 3:
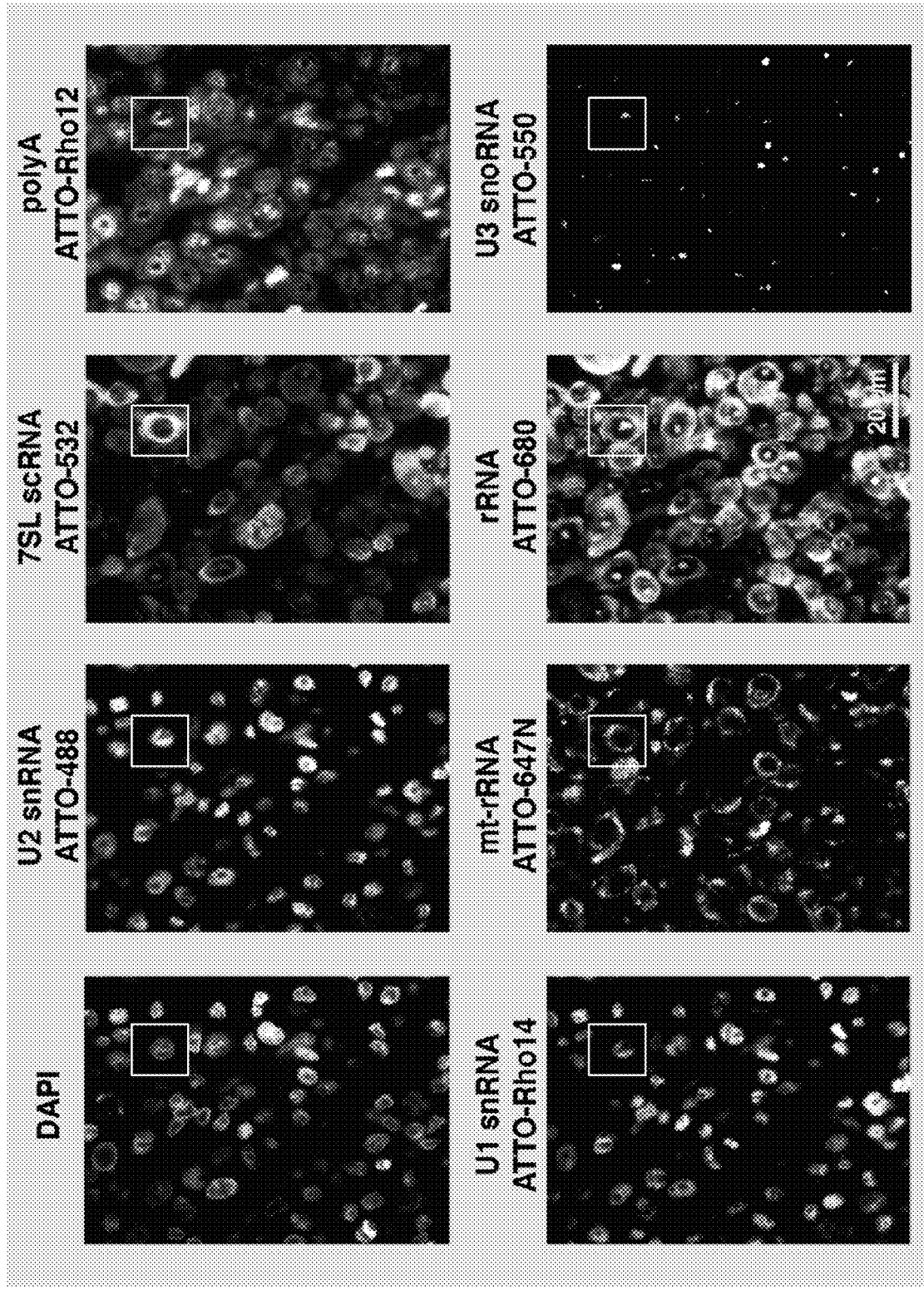

As set forth herein, the multiplex FISH to be employed in context with the inventive method described and provided herein allows simultaneous determination of the presence of several RNA species as described herein. For example, in accordance with the present invention, an 8-color multiplex FISH may be applied as follows. FIG. 3 depicts 8-color multiplex FISH, enabling the simultaneous detection of 7 or more distinct fluorophores with partially overlapping spectra. Since those RNAs are abundant with distinct subcellular localizations (U1, U2 snRNA: nuclear, mt-RNA: mitochondrial, 7SL scRNA-cytoplasmic, U3 snoRNA: nucleolar, rRNA-nucleolar, poly(A): nuclear/cytoplasmic), the specificity of the signals may be visually determined (see red square showing specific signals on one cell, FIG. 3). Using spectral imaging with linear unmixing, it may be examined whether all individual signals within the entire spectrum (sum of all spectra) must be near-equal, which appears to be one of the most relevant limitations of current methods. The following parameters may be chosen in accordance with the present invention 1. The $T_M$-equalized specific probes are detectable in an additive fashion (signal intensity of 4 probes=4× intensity of single probe), which allows control of the number of probes per target (for too strong or too weak signal, number of probes may be decreased or increased, respectively). 2. When an increase in number of probes is not possible, a dye with stronger quantum yield may be used; 3. If stronger fluorophore is insufficient, twice the number of fluorophores per probe may be used. In addition, using directly labeled LNA/DNA probes without signal amplification, allows to accurately quantify signal intensity for each RNA target (cf. Table 1). Normalized relative RNA FISH intensities fully correlated with RNA sequencing data, indicating the quantification potential of the method described and provided in context with the present invention.

TABLE 1

Comparison of ncRNA small RNAseq sequencing counts and normalized intensity derived from RNA FISH. Read counts were determined using >2000 small RNA cDNA libraries from various tissues. All probes were conjugated to the same ATTO-550 dye and the intensity was measured using the same window size with ~200 cells. Poly(T) probe targeting poly(A) tails of mRNAs was conjugated to ATTO-647N, used in combination with other probes and poly(A) signal was subsequently used to normalize intensities as follows: Relative fluorescence intensity normalized to poly(A) = [measured intensity/(number of fluorophores in probe set * exposure time)]/[measured intensity/(number of fluorophores in poly(A) probe * exposure time).

| RNA category | Name | Transcript length (nt) | Read counts (×10$^6$) | Read counts/ transcript length | Normalized relative fluorescence intensity from RNA FISH |
|---|---|---|---|---|---|
| rRNA | 28S | 5 070 | 84..5 | 1.67E+04 | 11.13 |
| snRNA | U1 | 164 | 1.63 | 9.94E+03 | 4.48 |
| snoRNA | U3 | 217 | 2.08 | 9.60E+03 | 1.97 |
| snRNA | U2 | 188 | 1.57 | 8.35E+03 | 4.03 |
| mt-rRNA | 16S | 1 559 | 5.64 | 3.62E+03 | 2.08 |

TABLE 1-continued

Comparison of ncRNA small RNAseq sequencing counts and normalized intensity derived from RNA FISH. Read counts were determined using >2000 small RNA cDNA libraries from various tissues. All probes were conjugated to the same ATTO-550 dye and the intensity was measured using the same window size with ~200 cells. Poly(T) probe targeting poly(A) tails of mRNAs was conjugated to ATTO-647N, used in combination with other probes and poly(A) signal was subsequently used to normalize intensities as follows: Relative fluorescence intensity normalized to poly(A) = [measured intensity/(number of fluorophores in probe set * exposure time)]/[measured intensity/(number of fluorophores in poly(A) probe * exposure time).

| RNA category | Name | Transcript length (nt) | Read counts (×10$^6$) | Read counts/ transcript length | Normalized relative fluorescence intensity from RNA FISH |
|---|---|---|---|---|---|
| scRNA | 7SL | 299 | 0.75 | 2.51E+03 | 1.83 |
| mt-rRNA | 12S | 954 | 2.20 | 2.31E+03 | 2.08 |

In accordance with the present invention, signal quantification may be reached as exemplarily shown in Table 2 displaying 8 LNA/DNA probes targeting mouse 28S rRNA and their intensities in mouse brain cortex sections. The probes were designed to have similar binding affinity shown by similar $T_M$ that is at least 10-20° C. above hybridization temperature. Table 2 shows that all intensities are near-equal and also demonstrates that pooling all 8 probes yields a total signal intensity that is 8 times higher than that for an individual probe. The fluorescence signal intensity of all 8 probes pooled together (498472) was only 1.2 higher than the sum of all signal intensities coming for single probes (492126) showing the high accuracy. This linear increase indicates that if the probes have similar binding affinity and are not washed off during hybridization (when $T_M$ of the probes at least 10° C. higher than hybridization temperature), the inventive method can be used for accurate target quantitation.

TABLE 2

Mouse 28S rRNA probe sequences.

8 oligonucleotide probes were designed to detect mouse 28S rRNA in neurons of mouse brain cortex using RNA FISH; LNA residues are indicated in lowercase letters. Signal intensities were recorded for each probe separately, in combination (rRNA1-8), and in their absence (blank). Signal intensity for each probe was ca. 100 times higher than that of the blank control. Pooling all 8 probes yielded a signal intensity that was 8x higher than that for an individual probe, indicating that RNA FISH can be used for accurate target quantitation (Σ[rRNA1, . . . , rRNA8] = 492126). Melting temperatures ($T_M$) for select probes are shown; $T_M$ was measured using 50% formamide, 1M NaCl, 50 mM phosphate (pH 7.0). All probes (100 nM) were hybridized at 55° C. for 16 h in hybridization buffer containing 50% FA and 1M NaCl N > 100 cells.

| Probe | Length (nt) | rRNA sequence (mmu 28S rRNA) | Position | LNA sequence | Intensity (AU) | Tm (° C.) |
|---|---|---|---|---|---|---|
| Blank | | | | | 572 | |
| rRNA1 | 20 | SEQ ID NO: 1 | 57-76 | SEQ ID NO: 9 | 58320 | |
| rRNA2 | 17 | SEQ ID NO: 2 | 1731-1747 | SEQ ID NO: 10 | 57104 | 78.1 |
| rRNA3 | 20 | SEQ ID NO: 3 | 1798-1817 | SEQ ID NO: 11 | 67824 | |
| rRNA4 | 19 | SEQ ID NO: 4 | 1839-1857 | SEQ ID NO: 12 | 59983 | |
| rRNA5 | 15 | SEQ ID NO: 5 | 1897-1911 | SEQ ID NO: 13 | 58829 | 71.8 |
| rRNA6 | 18 | SEQ ID NO: 6 | 2193-2210 | SEQ ID NO: 14 | 63003 | 71.3 |
| rRNA7 | 16 | SEQ ID NO: 7 | 3918-3933 | SEQ ID NO: 15 | 61460 | |
| rRNA8 | 17 | SEQ ID NO: 8 | 4249-4265 | SEQ ID NO: 16 | 65603 | 70.6 |
| rRNA1-8 | | All probes pooled together | | | 498472 | |

The term "hybridization" or "hybridizes" as used herein in context with nucleic acid molecules/sequences incl. miRs, mRNAs, DNAs, cDNAs, LNAs, and others as described herein, or a portion or fragment thereof may relate to hybridizations under stringent, low stringent or non-stringent conditions. In one embodiment, the conditions are preferably stringent. Said hybridization conditions may be established according to conventional protocols described, for example, in Sambrook, Russell "Molecular Cloning, A Laboratory Manual", Cold Spring Harbor Laboratory, N. Y. (2001); Current Protocols in Molecular Biology, Update May 9, 2012, Print ISSN: 1934-3639, Online ISSN: 1934-3647; Ausubel, "Current Protocols in Molecular Biology", Green Publishing Associates and Wiley Interscience, N. Y. (1989), or Higgins and Hames (Eds.), "Nucleic acid hybridization, a practical approach", IRL Press Oxford, Washington DC, (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. ("stringent conditions" as used herein). Non-stringent hybridization conditions for the detection of homologous or not exactly complementary sequences may be set at 6×SSC, 1% SDS at 65° C. ("non-stringent conditions" as used herein). As is well known, the length of the probe and the composition of the nucleic acid to be determined constitute further parameters of the hybridization conditions. Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. In accordance to the invention described herein, low stringent hybridization conditions for the detection of homologous or not exactly complementary sequences may, for example, be set at 6×SSC, 0.5% SDS at 65° C. ("low stringent conditions" as used herein). As is well known, the length of the probe and the composition of the nucleic acid to be determined constitute further parameters of the hybridization conditions.

Hybridizing nucleic acid molecules also comprise fragments of the above described molecules. Such fragments may represent nucleic acid molecules serving as inhibitors as described herein or a functional fragment thereof. Furthermore, nucleic acid molecules, which hybridize with any of the aforementioned nucleic acid molecules, also include complementary fragments, derivatives and variants of these molecules. Additionally, a hybridization complex refers to a complex between two nucleic acid sequences (e.g., cDNA/LNA) by virtue of the formation of hydrogen bonds between complementary G and C bases and between complementary A and T (or U for RNA as known to the skilled person) bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms "complementary" or "complementarity" refer to the natural binding of polynucleotides under permissive salt and temperature conditions by base-pairing. For example, the sequence "A-G-U" binds to the complementary sequence "U-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

Having performed RNA FISH as described herein, it is preferred that a sample is stained with hematoxylin and eosin after FISH of RNA was performed.

As described herein, in the context of the methods of the present invention, inter alia, 28S rRNA and poly(A) RNA are determined by FISH as control. This control, i.e., 28S rRNA and poly(A) RNA are of particular interest as control, since the ratio between poly(A) RNA and 28S rRNA is indicative of the potential degradation of RNA in a sample. Accordingly, it is preferred that prior to performing step(a) and/or step(b) of said method, said sample is checked for the ratio between poly(A) (m)RNA and 28S rRNA.

Figure 5:
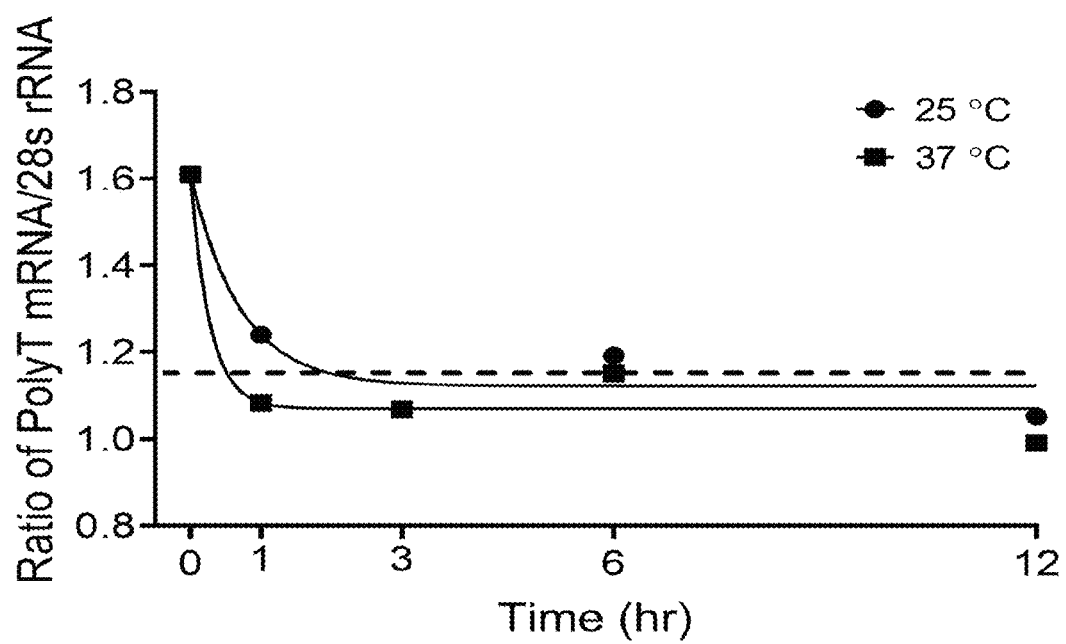

Indeed, the present inventors observed that a quality control of a sample as described herein prior to performing multiplex RNA FISH and/or multiplex RNA sequencing may be helpful. Surprisingly, the present inventors found that effects on RNA degradation are reflected by the ratio of PolyA (m)RNA/28S rRNA. As is shown in FIG. 5, the ratio (fluorescence activity/units) of PolyA (m) RNA/28S rRNA can be used to assess RNA degradation in samples, e.g., formalin-fixed paraffin-embedded (FFPE) tissue section samples, with ratios below 1 signifying degraded RNA (as a perhaps ideal ratio 1.15 is marked as dotted line in FIG. 5).

Accordingly, it is preferred that prior to performing multiplex RNA FISH (step (a) as referred to herein) and/or multiplex RNA sequencing (step(b) as referred to herein) in the context of the methods of the present invention, a sample as described herein is checked whether the ratio between polyA (m)RNA and 28S rRNA is 1:1 or greater than 1:1, e.g. 1.05:1, 1.1:1, 1.15:1, 1.2:1, 1.3:1, 1.4:1, 1.5:1, 2:1 or 3:1.

However, in the alternative, it is preferred that prior to performing multiplex RNA FISH (step (a) as referred to herein) and/or multiplex RNA sequencing (step(b) as referred to herein) in the context of the methods of the present invention, a sample as described herein is checked whether the ratio between polyA (m)RNA and 28S rRNA is 1:1 or lower than 1:1, e.g. 1:1.05, 1:1.1, 1:1.15, 1:1.2, 1:1.3, 1:1.4, 1:1.5, 1:2, or 1:3.

As described herein, according to the method provided by the present invention, following the multiplex FISH step, a multiplex sequencing step follows (step (b)). Accordingly, after the FISH step, a sequencing step is performed in order to confirm the result of step (a) (multiplex FISH) and/or to determine the presence of additional biomarkers indicative for the respective disease. That is, in context with the present invention, the same biomarkers may be sequenced in step (b) whose presence has been determined in step (a), or other or additional biomarkers than those of step (a) may be sequenced in step (b). In one embodiment of the present invention, the same biomarkers may be sequenced in step (b) whose presence has been determined in step (a). The sequencing of the biomarkers may be performed by methods known in the art and as described and exemplified herein. For example, in accordance with the present invention, after tissue has been stained in step (a) during the FISH assay, and where the disease to be diagnosed is cancer (e.g., breast cancer), the tumor may be selectively isolated from normal tissue and immune cells by, e.g., laser micro-dissection. From the homogenous population of cancer cells, total RNA may then be extracted and subjected to RNAseq (cf. Cánovas et al., Sci Reports (2014), 4 (art. no. 5297), doi: 10.1038/srep05297) to confirm quantification of the first analysis (visualization in multiplex FISH of step (a)) and to reveal the presence and quantity of the same or even a much broader panel of specific biomarkers. Accordingly, in the context of the methods of the present invention, it is preferred that RNA is extracted from a sample when multiplex sequencing of RNA is performed. Preferably, RNA extraction is done as described in the appended examples. The sequencing of different RNA markers as described may be based on suitable cDNA libraries (DNA synthetized from RNA population used as template for sequencing) known in the art (e.g., Illumina TrueSeq cDNA library, or ClontechSMART cDNA library as described, e.g., in www.takarabio.com/products/cdna-synthesis/cdna-synthesis-kits/library-construction-kits). Sequencing may generally be done by RNA sequencing methods known in the art and as inter alia described in, e.g., Illumina TrueSeq cDNA library preparation protocol (support.illumina.com/content/dam/illumine-support/documents/documentation/chemistry_documentation/samplepreps_truseq/trusegrna/truseq-rna-sample-prep-v2-guide-15026495-f.pdf). Preferably, RNA sequencing is done as described in the appended examples.

As described above, in the context of multiplex sequencing of RNA, a cDNA library may be prepared. Accordingly, it is preferred that for the preparation of a cDNA library 3-adapter molecules comprising a barcode are used. Preferably, these 3-adapter molecules comprising a barcode are preadenylated. It is also preferred that these 3-adapter molecules comprising a barcode are a collection. These 3-adapter molecules comprising a barcode, which may preferably be preadenylated, are either pooled or unpooled, with pooled being preferred. To be more precise, the collection of these 3-adapter molecules comprising a barcode, which may preferably be preadenylated, may preferably be pooled or unpooled, with a pooled collection being preferred. Such a collection comprises at least 2, 3, 4, 5, 6, 7, 8, 9, 10, 11, 12, 13, 14, 15, 16, 17, 18, 19, 20, 21, or more 3-adapter molecules comprising a barcode and which may preferably be preadenylated.

Indeed, much to their surprise, the present inventors observed when using 3-adapter molecules for the preparation of a cDNA library in the context of performing multiplex RNA sequencing that 3-adapter molecules comprising a barcode reduce ligation and technical biases in RNA sequencing. In fact, in contrast to the present invention, the preparation of cDNA libraries for RNA sequencing in the prior art is made by using 3-adapter molecules not having a barcode. For cDNA library preparation as done in the prior art, the barcode is only ligated later during the preparation of the cDNA library.

As is shown in FIG. 7, cDNA libraries generated using standard 3-adapters (sample I-1-I-3) when compared to cDNA libraries using 3-adapters comprising a barcode, e.g., pooled MDX barcoded pre-adenylated 3'-adapters) (MDX-4a-c) unpooled MDX barcoded pre-adenylated 3'-adapters (MDX-7-MDX-9) do not reduce ligation bias as shown by density estimates that are closer to the expected read counts (denoted as dotted line at 0), whereas 3'-adapters used in the context of the methods of the present invention, which comprise a barcode and which may preferably be preadenylated, reduce ligation bias as shown by density estimates that are closer to the expected read counts (denoted as dotted line at 0). Hence, the 3' adapters of the present invention are advantageous for the preparation of a cDNA library when performing multiplex RNA sequencing. This advantage could not have been expected.

The present invention further relates to a kit for performing the method as described and provided herein.

Preferably, the kit comprises glass slides, preferably positively charged glass slides, frame slides, frame slides with PET membrane, or glass slides with membrane. It is also preferred that the kit further comprises formaldehyde and/or paraffin, The kit may preferably also comprise EDC or ETT and/or hematoxylin and/or eosin.

The kit may preferably also comprise siliconized nuclease-free containers.

Moreover, the kit preferably further comprises probes for fluorescence in situ hybridization of RNA and/or 3'-adapter molecules comprising a barcode for preparing a cDNA library from RNA. These 3'-adapter molecules comprising a barcode which may be comprised by the kit are preferably preadenylated.

The probes for RNA FISH preferably comprised by the kit may preferably be specific for HER2, ER, PR, NUPR1, CSF1, GRB7, Ki-67, STK15, Survivin, Cyclin B1, MYBL2, ER, PR, Bcl2, SCUBE2, Stromelysin 3, Cathepsin L2, GSTM1, BAG1, and CD68.

Also, the probes for RNA FISH preferably further comprised by the kit may preferably be specific for miR-21, miR-29a, miR-221, and miR-375.

Similarly, the probes for RNA FISH preferably further comprised by the kit may preferably be specific for U2 snRNA and/or 7SL scRNA.

Preferably, as control, the kit may also comprise probes which are specific for 28S rRNA, poly(A) RNA, Beta-actin, GAPDH, RPLPO, GUS, TFRC.

It is also preferred that the 3'-adapter molecules comprising a barcode which may be comprised by the kit are a collection of 3'-adapter molecules comprising a barcode.

Preferably, the 3'-adapter molecules comprising a barcode comprised by the kit are pooled or unpooled, with unooled being preferred.

The present invention further relates to the use of such a kit.

The embodiments, which characterize the present invention, are described herein, shown in the Figures, illustrated in the Examples, and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

The term "and/or", wherever used herein, includes the meaning of "and", "or" and "all or any other combination of the elements connected by said term".

The term "about" or "approximately" as used herein means within 20%, preferably within 10%, more preferably within 5%, and most preferably within 3% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

Unless specifically stated otherwise, in each instance herein any of the terms "comprising", "consisting essentially of" and "consisting of" may be replaced with either of the other two terms. For example, where a given feature, compound or range is indicted as "comprised by" a respective broader term, such broader term may also "consist of" such feature, compound or range.

It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

Figure 1:
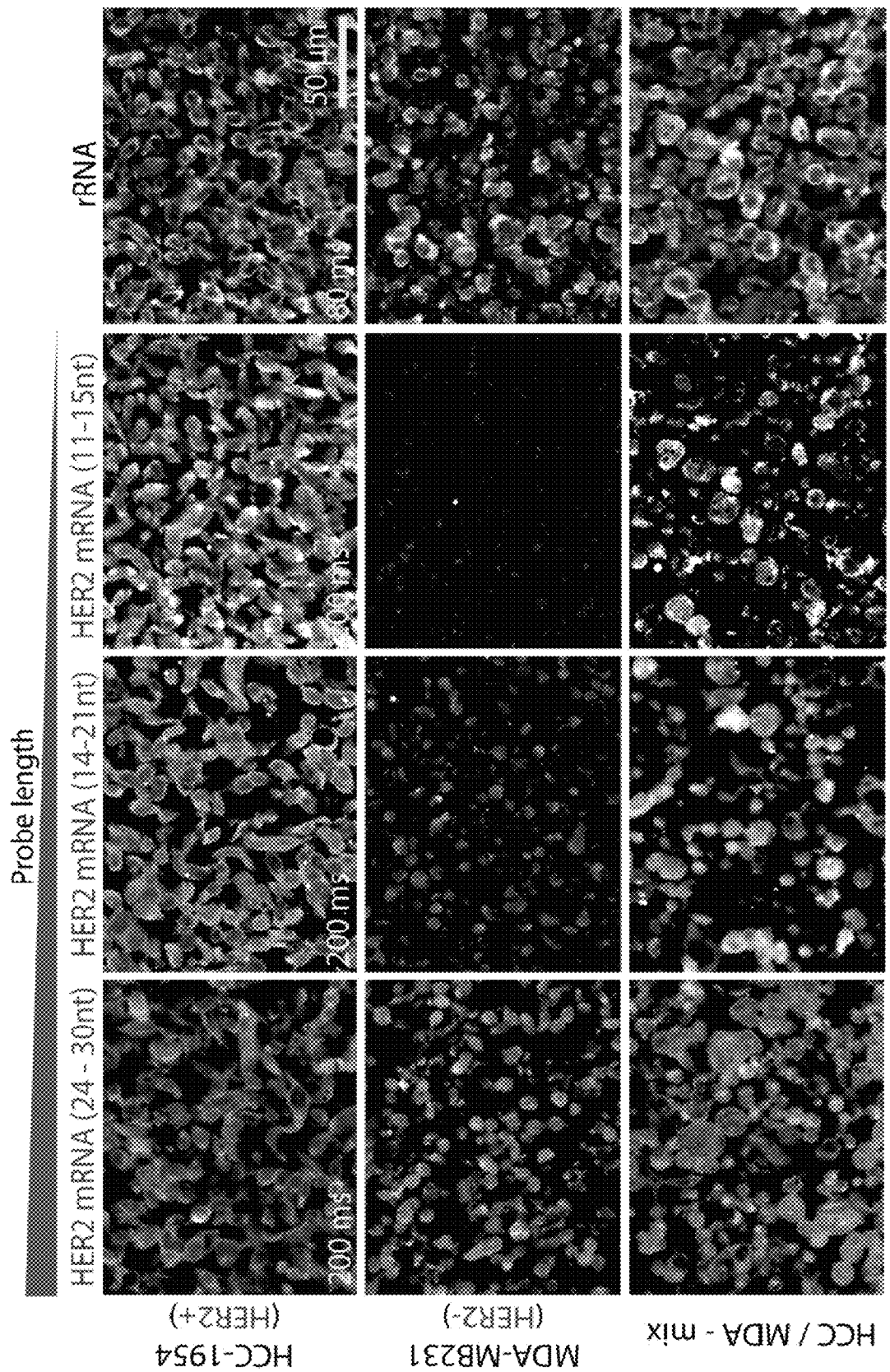

The Figures show:

FIG. 1 Differentiating FFPE breast cancer cell lines using RNA FISH and shorter DNA probes. 45 DNA (24 to 30-nt), 39 DNA (14 to 21-nt) or 53 (11 to 15-nt) LNA/DNA probes conjugated to ATTO-550 were used to differentiate HER2 positive (HCC-1954) and HER2-negative (MDA-MB231) breast cancer cell lines, stained and visualized in parallel. Five rRNA probes were conjugated to ATTO-488. Probes were hybridized using 25% Formamide and 1M NaCl at 40° C. HCC-1954 cell line could not be distinguished from MDA-MB231 due to rRNA mishybridization of DNA probes. However, LNA/DNA probes finally discriminate between HER2+ and HER2− cells, indicating these probes being specific. Exposure times for rRNA and HER2 were 80 ms and 200 ms, respectively. Scale bar, 50 µm.

FIG. 2 in situ click labeling. Exemplary set-up. Two short fluorophore-labeled neighbouring probes are tagged with azide and alkyne and fuse together by click chemistry. Following stringent wash, mishybridized probes are removed. $T_M$ was measured for each ca. 15-nt long LNA/DNA probe (in duplex with RNA). Both $T_M$s were similar, −50° C. in phosphate buffer containing 50% formamide/1M NaCl.

FIG. 3 RNA FISH of 6 ncRNAs, poly(A) RNA and DAPI nuclear DNA staining. RNA FISH was performed using the HCC-1954 cell line. We used 12 to 17 nt long LNA-modified DNA probes targeting U2 snRNA, 7SL small cytoplasmic (sc)RNA, U1 snRNA, mt-RNA, rRNA, U3 snoRNA and poly(T) probes targeting poly(A) conjugated to ATTO-488, ATTO-532, ATTO-Rho12, ATTO-Rho 14, ATTO-647N, ATTO-680 and ATTO-550, respectively. The cells were scanned using Vectra Intelligent Slide Analysis System (PerkinElmer).

FIG. 4 The MultiplexDX (MDX) method of sample processing in comparison to traditional (prior art) method of sample processing. The method of the present invention prevents diffusion of small RNA (e.g., microRNA) out of the cell, ensuring high concentrations of small RNA. Mouse brain tissue sections (10 µm) were obtained using a microtome from either formalin-fixed, flash-frozen (FFFF) tissues processed immediately (0 seconds, baseline control) or formalin-fixed, paraffin-embedded (FFPE) tissues processed after 5, 60, 180, and 600 seconds (s). Only the MDX paraffin ribbon was briefly placed in an ice-cold water bath, then a 42° C. water bath before being positioned on a glass slide after either 5 s (MDX method, data point enclosed in shaded box) or 60, 180, and 600 s (Other methods). Note that paraffin ribbons processed pursuant to traditional (prior art) methods were not placed in an ice-cold water bath after having been obtained from microtome sectioning. The tissue was deparaffinized, dried, and then microRNA was extracted using the Ambion® PureLink® miRNA Isolation Kit and the concentration of microRNA was measured using NanoDrop.

FIG. 5 Effects of RNA degradation. Effects of RNA degradation on the ratio of PolyA mRNA/28S rRNA (A) and on mean fluorescent intensity of PolyA mRNA expression (B) following incubation of rat liver tissue for 0, 1, 3, 6, and 12 hours at either room temperature (25° C.) or elevated temperature (37° C.). A, The ratio (fluorescence activity/units) of PolyA mRNA/28S rRNA can be used to assess RNA degradation in formalin-fixed paraffin-embedded (FFPE) tissues, with ratios below 1 signifying degraded RNA (as a perhaps ideal ratio 1.15 is marked as dotted line). B, Confocal photomicrographs of PolyA mRNA expression showing a reduction in fluorescent intensity across timepoints.

FIG. 6 Laser capture microdissection (LMD) reduces bias introduced by sampling heterogeneous tissues and ensures concordance between RNA fluorescent in situ hybridization (FISH, A) and RNA sequencing (B). A, RNA FISH reveals Her2 amplification in breast cancer biopsy tissue in patient A (left panel), but not patient B (right panel). B, Laser capture microdissection of Her2+ cell populations (approximately 100 cells shown in square inset) followed by RNA sequencing shows high concordance with Her2 expression assessed by RNA FISH. C, Whole tissue sampling followed by RNA sequencing demonstrates low concordance with RNA FISH due to sampling from heterogeneous cell populations. This could lead to inaccurate diagnosis of patient A's Her2 status and consequently inappropriate or ineffective treatment.

FIG. 7 Barcoded pre-adenylated 3'-adapters reduce ligation (A) and technical (B) biases in small RNA sequencing. A, Violin plots illustrating the density estimates of small RNA sequencing libraries prepared using the miRXplore Universal Reference containing an equimolar pool of 962 unique microRNA sequences. The libraries were generated using standard competitor-I 3'-adapters (sample I-1-I-3), pooled MDX barcoded pre-adenylated 3'-adapters (MDX-4a-c) or unpooled MDX barcoded pre-adenylated 3'-adapters (MDX-7-MDX-9). MDX 3'-adapters, compared to competitor I 3'-adapters, reduce ligation bias as shown by density estimates that are closer to the expected read counts (denoted as dotted line at 0). B, Box-and-whisker plots demonstrate that pooling of MDX barcoded pre-adenylated 3'-adapters reduces technical biases observed in miR-21, miR-29a, miR-221, and miR-375 when using unpooled MDX barcoded pre-adenylated 3'-adapters. Note that pooled MDX barcoded pre-adenylated 3'-adapters are shown left, while unpooled MDX barcoded pre-adenylated 3'-adapters are shown right.

The following Sequences are provided herein:

```
SEQ ID NO: 1
Mus musculus (mmu)
RNA
GGAAAAGAAACTAACCAGGA

SEQ ID NO: 2
Mus musculus (mmu)
RNA
ATCAGACCCCAGAAAAG

SEQ ID NO: 3
Mus musculus (mmu)
RNA
CTAAGGAGTGTGTAACAACT

SEQ ID NO: 4
Mus musculus (mmu)
RNA
CTGAAAATGGATGGCGCTG

SEQ ID NO: 5
Mus musculus (mmu)
RNA
CGGAACGGGACGGGA

SEQ ID NO: 6
Mus musculus (mmu)
RNA
AGTCGGTCCTGAGAGATG

SEQ ID NO: 7
Mus musculus (mmu)
RNA
GGAGCAGAAGGGCAAA

SEQ ID NO: 8
Mus musculus (mmu)
RNA
TCAGTACGAGAGGAACC

SEQ ID NO: 9
artificial
LNA
LNA residues are indicated in lowercase letters
TCcTGGtTAgTTtCTtTTCC SEQ ID NO: 10
artificial
LNA
LNA residues are indicated in lowercase letters
CttttTCtGggGTcTGaT SEQ ID NO: 11
artificial
LNA
LNA residues are indicated in lowercase letters
AGTtGTtACACAcTCcTtaG SEQ ID NO: 12
artificial
LNA
LNA residues are indicated in lowercase letters
CAGcGCcATcCAtTTTcCAG SEQ ID NO: 13
artificial
LNA
LNA residues are indicated in lowercase letters
TCCcGTcCCgTTCCG SEQ ID NO: 14
artificial
LNA
LNA residues are indicated in lowercase letters
CATCTcTcAGGAcCgAcT SEQ ID NO: 15
artificial
LNA
LNA residues are indicated in lowercase letters
TtTGCCcTTCTGCtCc SEQ ID NO: 16
artificial
LNA
LNA residues are indicated in lowercase letters
GGTtCctCtCGtACTgA
```

The present invention may also be characterized by the following items:

1. A method for diagnosing a disease, said method comprising:
   (a) determining by multiplex fluorescence in situ hybridization (FISH) whether or not mRNA species and/or at least three miRNA species of disease-associated biomarkers are present in a sample obtained from a subject; and
   (b) determining by multiplex sequencing whether or not said mRNA species of disease-associated biomarkers and/or said miRNA species of disease-associated biomarkers of step(a) are present in said sample.
2. The method of item 1, wherein step(a) further comprises determining by multiplex FISH whether or not snRNA species and/or scRNA species of disease-associated biomarkers are present in said sample.
3. The method of any one of the preceding items, wherein step(b) further comprises determining by multiplex sequencing whether or not snRNA and/or scRNA species of disease-associated biomarkers are present in said sample.
4. The method of any one of the preceding items, wherein the presence of said disease-associated biomarkers in step(a) and step(b) is indicative of said disease.
5. The method of any one of the preceding items, wherein said method allows the diagnosis of a disease on the presence or absence of said disease-associated biomarkers.
6. The method of any one of the preceding items, wherein said disease is cancer.
7. The method of item 6, wherein said cancer is breast cancer.
8. The method of any one of the preceding items, wherein said mRNA is selected from the group consisting of HER2, ER, PR, NUPR1, CSF1, GRB7, Ki-67, STK15, Survivin, Cyclin B1, MYBL2, ER, PR, Bcl2, SCUBE2, Stromelysin 3, Cathepsin L2, GSTM1, BAG1, and CD68.
9. The method of any of the preceding items, wherein said miRNA is selected from the group consisting of miR-21, miR-29a, miR-221, and miR-375.
10. The method of any one of the preceding items, wherein said snRNA is U2 snRNA.
11. The method of any one of the preceding items, wherein said scRNA is 7SL scRNA.

12. The method of any one of the preceding items, wherein additionally one or more RNAs selected from the group consisting of 28S rRNA, poly(A) RNA, Beta-actin, GAPDH, RPLPO, GUS, TFRC are determined by FISH as control.
13. A kit for performing the method of any one of the preceding items.
14. Use of a kit of item 13 for performing the methods of any one item 1 to 12.

The invention is further illustrated by the following examples, however, without being limited to the example or by any specific embodiment of the examples.

EXAMPLES

Test of Probe Design

To test an RNA FISH probe design and compare to other commercially available design, two breast cancer cell lines were used, HER2+(HCT1954) and HER2− (MDA-MB231). Stellaris probe design program (Biosearch Technologies) was used to prepare ERBB2 mRNA probes. Instead of 20-nt long probes, forty five 24 to 30-nt long DNA probes were designed to increase binding affinity, length of the probes varied to equalize $T_M$s (resulting $T_M$s varied between 48.1 and 56.9° C. in 50% Formamide (FA), 1 M NaCl, 50 mM phosphate (pH 7.0)). The GC content was limited between 50 to 64% as suggested by Stellaris. In subsequent RNA FISH, rRNA probes were also used as an internal control and standard for signal specificity and RNA content. Subsequently, DNA probes (24 to 30-nt long) were shortened either from 5'-end or 3'-end to avoid rRNA mishybridization (no segment longer than 8 nt with rRNA sequence complementarity) to yield 39 shorter DNA probes (14 to 21-nt long). Melting temperatures of these DNA probes varied from 38.8 to 47.1° C. While small discrimination between HER2+ and HER2− breast cancer cell was observed, rRNA mishybridization was still predominant. To avoid mishybridization and increase probe specificity, 53 short (11- to 15-nt long) directly labeled LNA-modified DNA (LNA/DNA) oligonucleotide probes were synthesized for ERBB2 mRNA with no longer than 6-nt sequence segment that cross-hybridize to the most abundant RNAs (rRNAs, tRNAs, snRNAs, mitochondrial rRNAs, etc.) using the RNA FISH probe design as described herein. Melting temperatures of these LNA/DNA probes varied from 44.2 to 52.1° C. These LNA/DNA probes were finally shown to be specific and distinguished HCC-1954 (HER2+) from MDA-MB231 (HER2-) breast cancer cells (cf. FIG. 1). Moreover, when comparing signal intensities of 100 cells from mRNA FISH and copy numbers of ERRB2 transcript from mRNA deep sequencing of those two HER2+ and HER2− cell line, the difference from mRNA FISH was 51-fold compared to 49-fold difference from mRNA sequencing. This indicates that very high specificity was achieved.

RNA Fish:

NOTE 1: Proteinase K permeabilization, 4% PFA fixation, acetylation and blocking endogenous biotin steps may be omitted.

NOTE 2: If FFFF (formaldehyde-fixed, fresh-frozen) tissues are used, after thawing and air-drying, incubate slides in 50 ml of 1-Methylimidazole buffer (pH 8.0) for 2 min at 25° C. and immediately start EDC fixation proceeding to step 14.

Microtome Sectioning

1 Paraffin blocks were trimmed to an optimal cuffing surface including the sample.

2 5 µm slices were cut; a brush was used to draw the section onto the knife holder.

3 Paraffin ribbon or section (slice) was placed in ice-cold water bath with a 2nd wet brush (it may expand, and wrinkles will vanish).

4 Swimming paraffin section was fished out using a glass slide, the paraffin ribbon was placed in a 42° C. water bath until it expanded and wrinkles vanished and then the paraffin section was fished out with a 2nd wet brush to position the section. NOTE: Using higher temperature of water bath than 42° C., can cause diffusion of especially short RNAs from the tissue due to paraffin melting.

5 Sections were dried at room temperature for at least 1 h until the glass slides were completely dry and water trapped between the tissue and glass slide has evaporated.

6 Sections were baked at 56° C. for 1 h.

Deparaffinization

7 Slides were incubated in 50 ml of Histo-Clear II twice for 5 min at 25° C.

8 Slides were incubated in 50 ml 100% ethanol for 2 min at 25° C.

9 Slides were incubated in 50 ml of 95% ethanol twice for 1 min at 25° C.

10 Slides were incubated in 50 ml of 70% ethanol for 1 min at 25° C.

11 Slides were incubated in 50 ml of 50% ethanol for 1 min at 25° C.

12 Slides were held in the Coplin jar under running cold tap water to rinse.

Fixation of Tissues with EDC/5-ETT

NOTE 3: EDC fixation can be omitted when long RNAs (mRNAs and rRNAs) are targeted, but one must be sure that the tissue used was well preserved and does not contain high levels of hydrolyzed RNA.

NOTE 4: For targeting tRNAs containing 5'-phosphate, EDC fixation would be advantageous.

13 Slides were incubated in 50 ml of 1-Methylimidazole buffer (pH 8.0) for 2 min at 25° C. This step was to remove residual 1×TBS buffer.

14 Fresh EDC/5-ETT solution was made prior to use.

15 In a humidified chamber, slides were placed face up in a slide rack. 1-Methylimidazole buffer (pH 8.0) was removed by tilting the slide and decanting the solution. In a humidified chamber, slides were placed face up in a slide rack.

16 500 µl of EDC/5-ETT solution was added to each slide and samples were incubated for 3 h at 50° C. in a sealed humidified chamber.

Wash Steps after Fixation

17 The samples were washed twice with 50 ml of 1×TBS for 3 min at 25° C.

Pre-Hybridization and Hybridization of Probe and RNA

18 Slides were placed with the tissue side up on a slide rack in a humidified chamber.

19 500 µl of freshly prepared hybridization buffer was added to each slide within the hydrophobic barrier. Tissue was fully covered. Slides were incubated in a sealed humidified chamber for 1 h at 25° C.

20 Hybridization buffer was removed by tilting the slide and decanting the solution.

Preparing the Probe and Hybridization

21 The desired probes were selected and ovens pre-heated to the appropriate hybridization temperature—approximately 20° C. below the $T_M$.

22 500 μl hybridization solution containing probes was added to each slide. Concentration of mRNA probes: 4 nM, abundant ncRNA: 10 nM, rRNA probes: 20 nM.

23 Slides were incubated in a sealed humidified chamber for 6 to 16 h at the hybridization temperature (37-50° C.).

Post-Hybridization Washes

24 Samples were washed two times in a glass Coplin jar filled with 50 ml of Wash buffer 1 for 5-10 min at 25° C. NOTE: When hybridization buffer (50% FA) is used, use Wash buffer 1 (50% FA), but when hybridization buffer (25% FA) is used, use Wash buffer 1 (25% FA).

25 Samples were washed in 50 ml of Wash buffer 2 for 5 min at 25° C.

26 Samples were rinsed in 50 ml of 1×TBS-T buffer for 3 min at 25° C.

In Situ Click Chemistry Cross-Linking

27 In an Eppendorf tube (for one slide), a solution of 63 μl of 20 mM $CuSO_4$ and 125 μl of 50 mM ligand THPTA was prepared. The final concentration of copper in the tube was 0.25 mM and the final concentration of ligand 1 in the tube was 1.25 mM (ligand to copper ratio, 5:1).

28 250 μl of 100 mM sodium ascorbate was added. The final concentration of sodium ascorbate in the tube was 5 mM.

29 The tube was closed and mixed by inverting the tube several times (to prevent more oxygen from diffusing in).

30 400 μl of freshly prepared $CuSO_4$/THPTA/sodium ascorbate solution was added to each slide.

31 Slides were incubated in a sealed humidified chamber avoiding light for 1 to 2 h at room temperature.

32 Samples were washed twice with 50 ml of 1×TBS-T for 3 min at 25° C.

Stringency Wash, if Desired 32a 1 ml wash buffer was added to each slide. Slides were incubated for 5-10 min at 40-50° C. (or 0-10° C. above previous hybridization temperature) in a sealed humidified chamber. Note: When hybridization buffer (50% FA) is used, use Wash buffer 1 (50% FA), but when hybridization buffer (25% FA) is used, use Wash buffer 1 (25% FA).

32b Samples were washed in 50 ml of wash buffer 2 for 5 min at 25° C.

32c Samples were rinsed in 50 ml of 1×TBS-T buffer for 3 min at 25° C.

Mounting Slides for Microscopy

33 Slides were placed horizontally, face up in a humidified slide rack and 500 μl of DAPI working solution was added to each slide for 10 min at 25° C.

34 Slides were washed two times in 50 ml of 1×TBS for 3 min at 25° C.

35 Slides were placed horizontally, face up in a humidified slide rack and 2 drops of mounting solution was added on the tissue section.

36 A glass coverslip was carefully placed over the tissue sections.

37 Cover slipped slides were air dried for 10 min.

38 Cover slipped slides were stored in a dark slide rack.

Fluorescence Slide Imaging

39 For use of Perkin Elmer Vectra 3.0 Quantitative Pathology Imaging System including slide scanning, RNA visualization, RNA biomarker quantification, spectral imaging, de-mixing, multiplexed visualization, whole-slide scanning, image analysis, etc., see User's Manual: www.perkinelmer.com/Content/LST Software Downloads/Vectra-User-Manual-3-0-3.pdf.

Laser Capture Microdissection: Tissue Microdissectioning and RNA Extraction 40 5-μm tissue sections previously stained and visualized by RNA FISH were stained with hematoxylin and eosin (H&E) for further pathological review.

41 Tissue part (region) of interest was identified by microscopy and comparing RNA FISH and H&E images, circled by imaging software, and these H&E slides were then laser microdissected by Leica LMD7 (see www.leica-microsystems.com/applications/life-science/laser-microdissection/).

42 Five to ten 5-μm sections were microdissected prior to RNA extraction in siliconized nuclease-free Eppendorf tube.

43 RNA extraction was performed on matched case-control specimens, the same day as tissue microdissection, to prevent tissue desiccation, RNA damage and technical differences.

44 500 μl of TRIzol@ Reagent was added to Eppendorf tube containing tissue pieces, and tissues were homogenized by pipetting up and down and tissues were incubated for 5 min at room temperature.

45 200 μl of chloroform was added, shaken vigorously (vortexing) for 15 seconds and the sample incubated at room temperature for 3 min.

46 The sample was centrifuged at 11,500 rpm (12,568×g) for 10 min at 4° C. using Sorvall fresco centrifuge.

47 After separation of the phases, the clear upper aqueous phase containing RNA was collected without disturbing the cloudy interphase or lower colored layer. pH of aqueous phase was set acidic (about 4)

48 The aqueous phase was transferred and divided into two fresh tubes, each containing approximately 500 μl of the lysate.

49 500 μl of ice-cold isopropyl alcohol was added to each of the tubes and incubated on ice for 30 min and centrifuged the samples at 11,500 rpm (12,568×g) for 10 min at 4° C.

50 The supernatant was removed. Then the tube was placed again into centrifuge in the same orientation, spun for another 10 s and the remaining liquid collected. For small pellets, washing of the pellet was not necessary.

51 For larger pellets, 500 μl of ice-cold 75% EtOH solution was added, the tube was inverted once without disturbing pellet, centrifuged to collect liquid at 11,500 rpm (12,568×g) for 10 min at 4° C.), liquid removed, and centrifuged again to remove residual liquid.

52 The supernatant was removed completely (i.e. use second 10 s spin). RNA samples were re-dissolved in 100 μl of Millipore water and the volumes recombined.

53 The RNA was quantified on a total RNA chip on a Bioanalyzer (Agilent, Danbury, CT, USA).

RNA Sequencing:

54 RNA sequencing of extracted RNA from microdissected tissue (1-2 μg) was performed using the Illumina TrueSeq cDNA library preparation protocol: support/documents/documentation/chemistry_documentation/samplepreps truseg/tru segrna/truseq-rna-sample-prep-v2-guide-15026495-f.pdf.

The invention claimed is:

1. A method for processing a biological sample, said method comprising:
 (a) performing multiplex fluorescence in situ hybridization (FISH) on a biological sample to determine presence of mRNA species in the biological sample, wherein the biological sample is a tissue section sample which is formaldehyde-fixed, fresh frozen tissue section or formaldehyde-fixed, paraffin embedded tissue section;
 (b) laser capturing cells of the biological sample having the mRNA species, wherein said laser capturing isolates the cells having the mRNA species from the biological sample, wherein said laser capturing comprises laser capture microdissection; and
 (c) performing multiplex sequencing of the mRNA species from the isolated cells of the biological sample.

2. The method of claim 1, wherein said sample is fixed prior to step (a), optionally said sample is fixed by treatment with 1-ethyl-3-(3-dimethylaminopropyl) carbodiimide (EDC) or 5-ethylthio-1H-tetrazole (ETT).

3. The method of claim 1, wherein said biological sample is a microtome sectioned paraffin embedded sample having been incubated at a temperature between 0° C. to 25° C.

4. The method of claim 1 wherein RNA is extracted from the cells after step (b) but before step (c).

5. The method of claim 1 wherein multiplex FISH signals are detected by microscopy.

6. The method of claim 1 comprising using a nucleic acid probe conjugated by click chemistry.

7. The method of claim 1, wherein step (a) and (b) forms a laser captured microdissected cells comprising the mRNA species hybridized to a nucleic acid probe attached to a fluorescence molecule.

8. The method of claim 1, wherein said mRNA species are selected from HER2, ER, PR, NUPR1, CSF1, GRB7, Ki-67, STK15, Survivin, Cyclin B1, MYBL2, ER, PR, Bcl2, SCUBE2, Stromelysin 3, Cathepsin L2, GSTM1, BAG1, and CD68.

9. The method of claim 1, wherein prior to performing step (a) and/or step (b) of said method, a ratio of polyA mRNA to 28S rRNA is determined.

10. The method of claim 1, wherein for multiplex sequencing of RNA a cDNA library is prepared by using 3'adapter molecules comprising a barcode, optionally said 3'-adapter molecules comprising a barcode are preadenylated.

11. The method of claim 9, wherein performing steps (a)-(c) or (b)-(c) is indicated if the ratio of poly A mRNA to 28S rRNA is 1:1 or greater than 1:1.

12. The method of claim 1 wherein two, three, four, five, six, seven, eight, nine, ten, or more than ten mRNAs are determined simultaneously.

13. The method of claim 12 wherein at least mRNA of HER2, ER, and PR mRNAs are determined simultaneously.

14. The method of claim 1 wherein step (a) further comprises (i) performing multiplex FISH on the biological sample to determine presence of one, two, three, four, five, six, seven, eight, nine, ten, or more than ten miRNA species, (ii) performing multiplex FISH on the biological sample to determine presence of snRNA (small nuclear RNA), (ii) performing multiplex FISH on the biological sample to determine presence of scRNA (small conditional RNA), or two or more of (i), (ii), and (iii).

15. The method of claim 1 wherein the tissue section sample is obtained from a tissue biopsy, optionally wherein the tissue biopsy is from breast tissue.

16. The method of claim 1 wherein step (b) reduces bias in results obtained by RNA FISH and/or RNA sequencing of the biological sample which is heterogeneous, increases concordance between RNA FISH and RNA sequencing, and/or reduces false-positive and/or false-negative results obtained by RNA FISH and/or RNA sequencing.

* * * * *